US012570746B2

(12) United States Patent
Chen et al.

(10) Patent No.:     US 12,570,746 B2
(45) Date of Patent:      Mar. 10, 2026

(54) ANTI-PD-L1 ANTIBODIES

(71) Applicant: WUXI BIOLOGICS IRELAND LIMITED, Dundalk (IE)

(72) Inventors: Yunying Chen, Shanghai (CN); Jing Li, Shanghai (CN)

(73) Assignee: WUXI BIOLOGICS IRELAND LIMITED, Dundalk (IE)

( * ) Notice: Subject to any disclaimer, the term of this patent is extended or adjusted under 35 U.S.C. 154(b) by 1030 days.

(21) Appl. No.: 17/761,127

(22) PCT Filed: Sep. 24, 2020

(86) PCT No.: PCT/CN2020/117351
§ 371 (c)(1),
(2) Date: Mar. 16, 2022

(87) PCT Pub. No.: WO2021/057836
PCT Pub. Date: Apr. 1, 2021

(65) Prior Publication Data
US 2022/0403031 A1      Dec. 22, 2022

(30) Foreign Application Priority Data
Sep. 25, 2019     (WO) ............... PCT/CN2019/107689

(51) Int. Cl.
*C07K 16/28*          (2006.01)
*A61P 35/00*          (2006.01)
*C12N 15/70*          (2006.01)

(52) U.S. Cl.
CPC .......... *C07K 16/2827* (2013.01); *A61P 35/00* (2018.01); *C12N 15/70* (2013.01); *C07K 2317/24* (2013.01); *C07K 2317/52* (2013.01); *C07K 2317/565* (2013.01)

(58) Field of Classification Search
CPC ............ C07K 16/2827; C07K 2317/24; C07K 2317/52; C07K 2317/565; C07K 2317/33; C07K 2317/56; C07K 2317/569; C07K 2317/64; C07K 2317/732; C07K 2317/76; C07K 2317/92; C07K 2317/94; A61P 35/00; C12N 15/70; A61K 2039/505; G01N 33/574
See application file for complete search history.

(56) References Cited

U.S. PATENT DOCUMENTS

| | | | |
|---|---|---|---|
| 10,556,954 B2 | 2/2020 | Ting et al. | |
| 2006/0115832 A1* | 6/2006 | Hoon | C12Q 1/6886 |
| | | | 435/6.16 |
| 2011/0190157 A1* | 8/2011 | Kipps | C12Q 1/6809 |
| | | | 506/17 |
| 2012/0178111 A1* | 7/2012 | Diamandis | G01N 33/57423 |
| | | | 435/7.1 |
| 2017/0022273 A1* | 1/2017 | Zhou | C07K 16/3023 |
| 2018/0291103 A1 | 10/2018 | Xu et al. | |
| 2019/0023793 A1 | 1/2019 | Shen et al. | |
| 2021/0002370 A1 | 1/2021 | Chen et al. | |

FOREIGN PATENT DOCUMENTS

| | | |
|---|---|---|
| CN | 109265548 A | 1/2019 |
| CN | 110003333 A | 7/2019 |
| CN | 110256564 A | 9/2019 |
| WO | WO 2017/020801 A1 | 2/2017 |
| WO | WO 2017/157334 A1 | 9/2017 |
| WO | WO 2018/024237 A1 | 2/2018 |
| WO | WO 2018/127709 A1 | 7/2018 |
| WO | WO 2018/233574 A1 | 12/2018 |
| WO | WO 2019/096121 A1 | 5/2019 |
| WO | WO 2019/158113 A1 | 8/2019 |

OTHER PUBLICATIONS

Rudikoff et al., Proceedings of the National Academy of Sciences USA, vol. 79, p. 1979-1983, 1982 (Year: 1982).*
Baxevanis et al., Expert Opinion: Drug Discovery, vol. 3, No. 4, p. 441-452, 2008 (Year: 2008).*
Cuzick et al., The Lancet, vol. 361, p. 296-300, 2003 (Year: 2003).*
Evans et al., Q. J. Med 1999: 92: 299-307 (Year: 1999).*
Komenaka et al., Clinics in Dermatology, 2004, vol. 22, p. 251-265, specifically p. 257 (Year: 2004).*
Hernandez-Ledesma et al., Peptides, vol. 30, p. 426-430, 2009 (Year: 2009).*
Schiffman et al., The New England Journal of Medicine, Vo. 353, No. 20, p. 2101-2104, 2005 (Year: 2005).*
Zhang et al., "Structural basis of a novel PD-L1 nanobody for immune checkpoint blockade", Cell Discovery, 2017, 3:17004, pp. 1-12.
Dougan et al., "Targeting Cytokine Therapy to the Pancreatic Tumor Microenvironment Using PD-L1-Specific VHHs", Cancer Immunology Research, 2018, 6(4): 389-401.

* cited by examiner

*Primary Examiner* — Nelson B Moseley, II
*Assistant Examiner* — Josephine K Darpolor
(74) *Attorney, Agent, or Firm* — James S. Keddie; Bozicevic, Field & Francis LLP

(57) ABSTRACT

Provided are anti-PD-L1 antibodies. It also provides the nucleic acid molecules encoding the anti-PD-L1 antibodies, expression vectors and host cells used for the expression of the anti-PD-L1 antibodies. It also provides the methods for producing the anti-PD-L1 antibodies and the use thereof.

18 Claims, 8 Drawing Sheets
Specification includes a Sequence Listing.

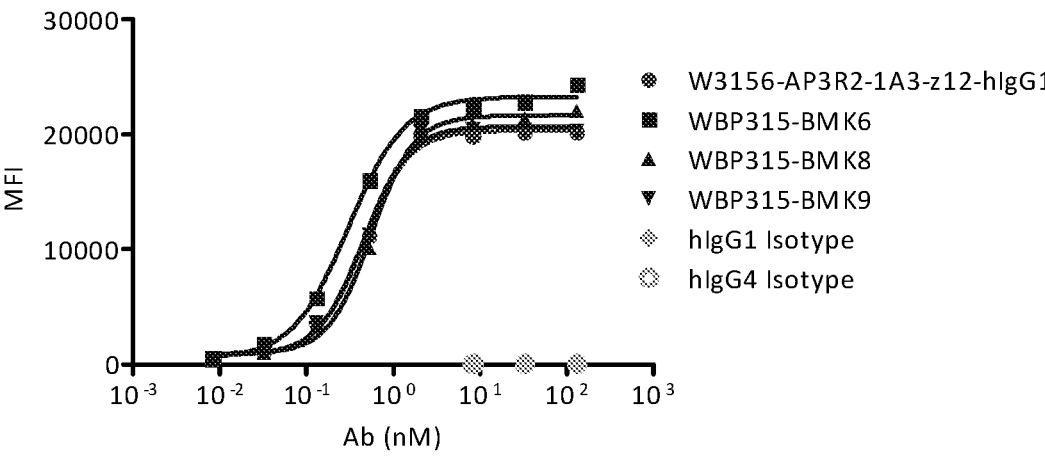
Figure 1A
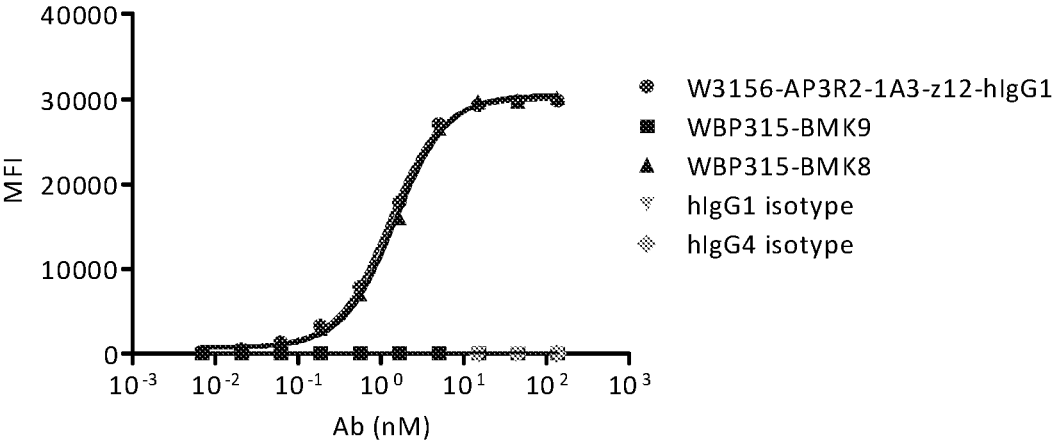
Figure 1B
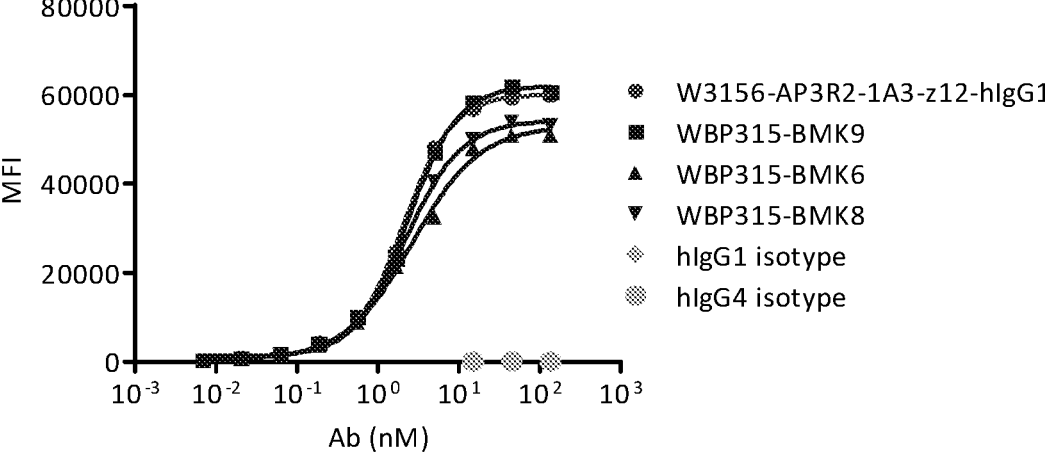
Figure 1C
Figure 1

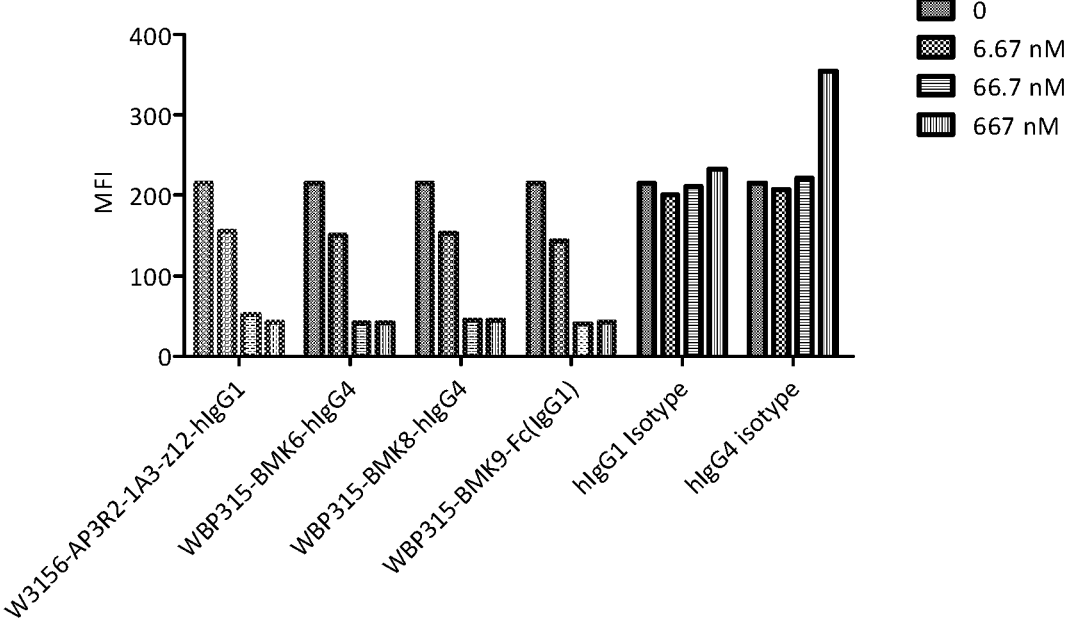
Figure 2C
Figure 2
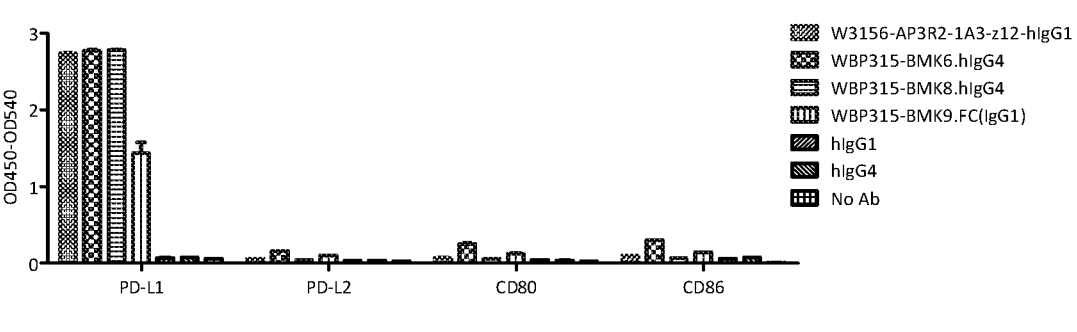
Figure 3

(A)

(B)

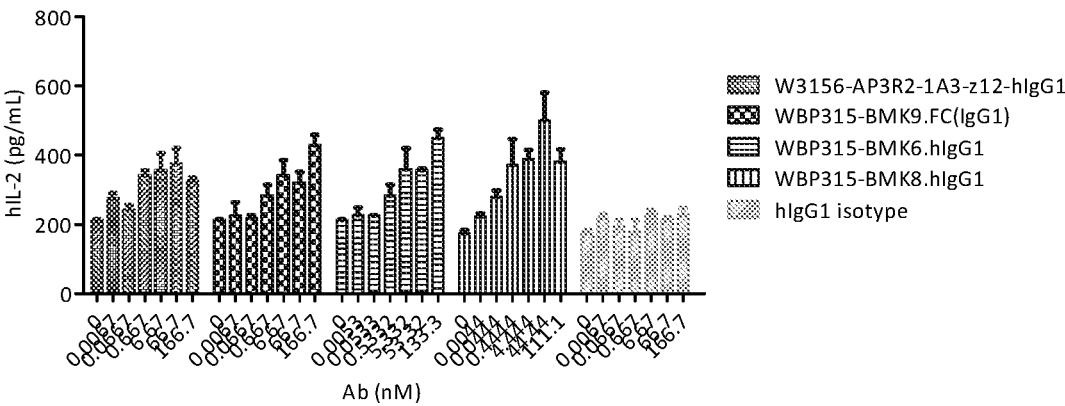
Figure 5A
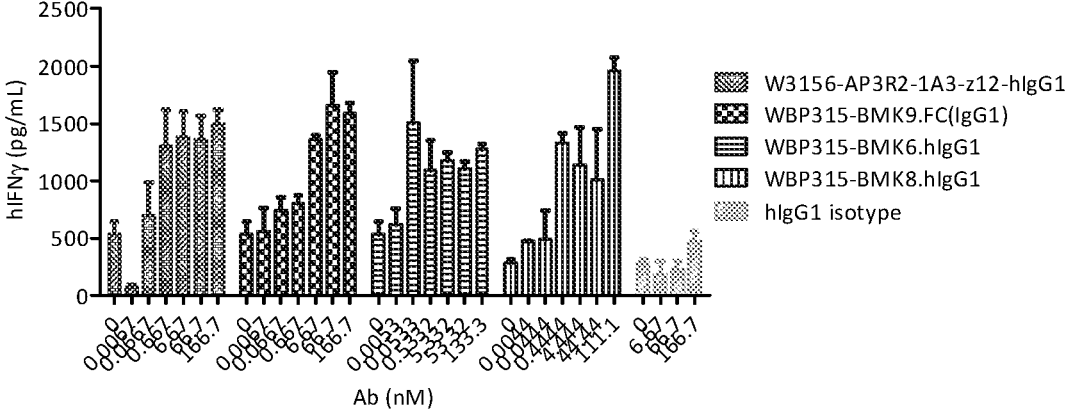
Figure 5B
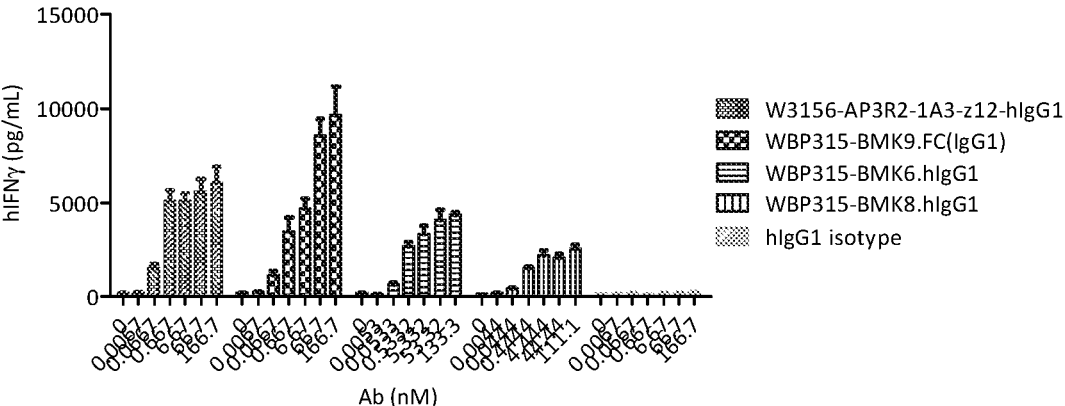
Figure 5C
Figure 5

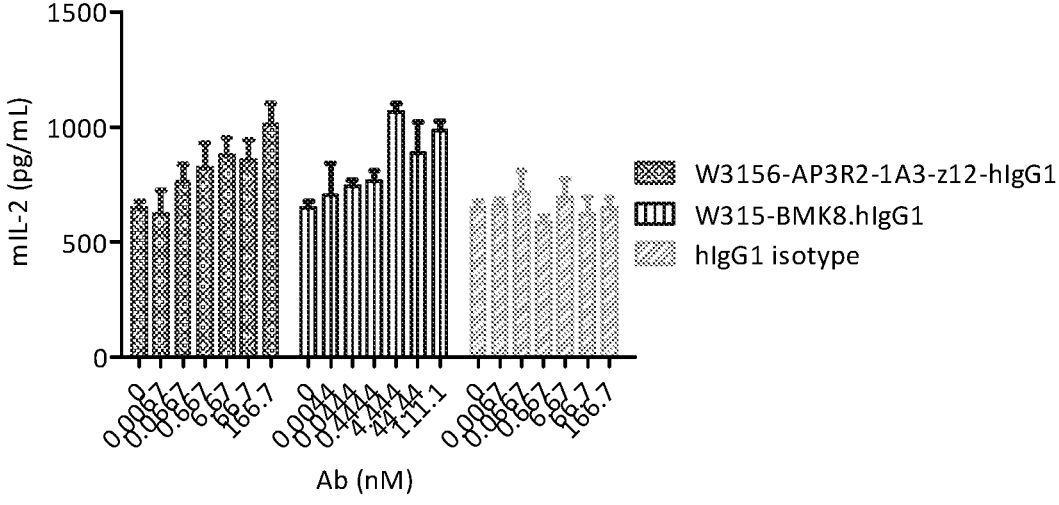
Figure 6A
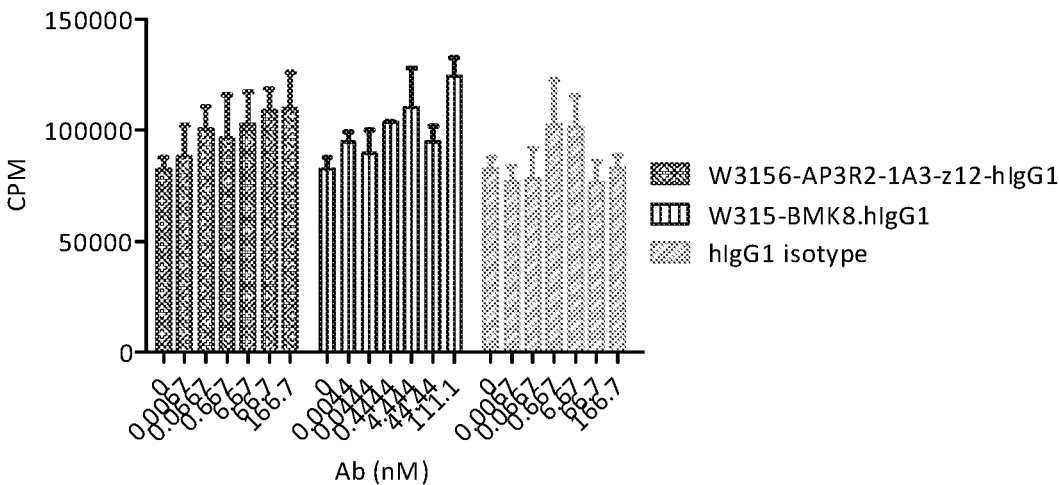
Figure 6B
Figure 6

- ● Herceptin+BT474 cells
- ※ W3156-AP3R2-1A3-z12-hIgG1
- ▲ W315-BMK6.uIgG1K(LFLEPS)
- ▼ W315-BMK8.uIgG1K(RKNA)
- ◆ W315-BMK9.FC(IgG1)
- ◌ hIgG1 Isotype

- ● Rituxuan+Raji cells
- ※ W3156-AP3R2-1A3-z12-hIgG1
- ◯ W315-BMK6.uIgG1K(LFLEPS)
- ▢ W315-BMK8.uIgG1K(RKNA)
- ◇ W315-BMK9.FC(IgG1)
- ▨ hIgG1 Isotype

SEQUENCE LISTING

```
<160> NUMBER OF SEQ ID NOS: 5

<210> SEQ ID NO 1
<211> LENGTH: 9
<212> TYPE: PRT
<213> ORGANISM: Artificial
<220> FEATURE:
<223> OTHER INFORMATION: CDR1

<400> SEQUENCE: 1

Gly His Phe Ser Asn Leu Ala Val Asn
1               5

<210> SEQ ID NO 2
<211> LENGTH: 17
<212> TYPE: PRT
<213> ORGANISM: Artificial
<220> FEATURE:
<223> OTHER INFORMATION: CDR2

<400> SEQUENCE: 2

Gly Ile Leu Trp Ser Gly Gly Ser Thr Phe Tyr Ala Asp Ser Val Lys
1               5                   10                  15

Gly

<210> SEQ ID NO 3
<211> LENGTH: 3
<212> TYPE: PRT
<213> ORGANISM: Artificial
<220> FEATURE:
<223> OTHER INFORMATION: CDR3
```

-continued

```
<400> SEQUENCE: 3

Gly Thr Asn
1

<210> SEQ ID NO 4
<211> LENGTH: 111
<212> TYPE: PRT
<213> ORGANISM: Artificial
<220> FEATURE:
<223> OTHER INFORMATION: full length

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly His Phe Ser Asn Leu Ala
            20                  25                  30

Val Asn Trp Phe Arg Gln Ala Pro Gly Lys Glu Arg Glu Leu Val Ala
        35                  40                  45

Gly Ile Leu Trp Ser Gly Gly Ser Thr Phe Tyr Ala Asp Ser Val Lys
    50                  55                  60

Gly Arg Phe Thr Ile Ser Arg Gly Asn Ala Glu Asn Met Leu Tyr Leu
65                  70                  75                  80

Gln Met Asn Ser Leu Arg Ala Glu Asp Thr Ala Val Tyr Tyr Cys Asn
                85                  90                  95

Thr Gly Thr Asn Trp Gly Gln Gly Thr Leu Val Thr Val Ser Ser
            100                 105                 110

<210> SEQ ID NO 5
<211> LENGTH: 333
<212> TYPE: DNA
<213> ORGANISM: Artificial
<220> FEATURE:
<223> OTHER INFORMATION: full length

<400> SEQUENCE: 5
gaggtgcagc tggtggagtc cggaggcgga ctggtgcagc ctggaggaag cctgagactg      60
agctgcgccg ctagcggcca cttcagcaac ctggccgtga actggttcag gcaggcccct     120
ggcaaggaga gggagctggt ggctggcatc ctgtggagcg gcggaagcac cttctacgcc     180
gacagcgtga agggcaggtt caccatcagc aggggcaacg ccgagaacat gctgtacctg     240
cagatgaact ccctgagggc cgaggacacc gccgtgtact actgcaacac cggcaccaac     300
tggggccagg gcacactcgt gaccgtgagc agc                                  333
```

ANTI-PD-L1 ANTIBODIES

CROSS-REFERENCE TO RELATED APPLICATIONS

The present application is a § 371 national phase of International Application No. PCT/CN2020/117351, filed on Sep. 24, 2020, which claims the benefit of PCT/CN2019/107689 filed on Sep. 25, 2019, all of which are entirely incorporated herein by reference.

SEQUENCE LISTING

The instant application contains a sequence listing and is hereby incorporated by reference in its entirety.

FIELD OF THE INVENTION

This application generally relates to antibodies. More specifically, the application relates to single-domain antibodies that specifically bind to PD-L1, a method for preparing the same, and the use thereof.

BACKGROUND OF THE INVENTION

Increasing evidences from preclinical and clinical results have shown that targeting immune checkpoints is becoming the most promising approach to treat patients with cancers.

The protein Programmed Death 1 (PD-1), an inhibitory member of the immunoglobulin super-family with homology to CD28, is expressed on T cells, activated B cells, and myeloid cells (Agata et al, supra; Okazaki et al (2002) Curr. Opin. Immunol. 14: 391779-82; Bennett et al. (2003) J Immunol 170:711-8) and has a critical role in regulating stimulatory and inhibitory signals in the immune system (Okazaki, Taku et al. 2007 International Immunology 19:813-824). PD-1 was discovered through screening for differential expression in apoptotic cells (Ishida et al (1992) EMBO J 11:3887-95).

PD-1 has two known ligands, PD-L1 (also named as B7-H1 or CD274) and PD-L2 (also named as B7-DC or CD273), which are cell surface expressed members of the B7 family (Freeman et al (2000) J Exp Med 192: 1027-34; Latchman et al (2001) Nat Immunol 2:261-8; Carter et al (2002) Eur J Immunol 32:634-43). Both PD-L1 and PD-L2 are B7 homologs that bind to PD-1, but do not bind to other CD28 family members.

The interaction of PD-1 expressed on activated T cells, and PD-L1 expressed on tumor cells negatively regulates immune response and damps anti-tumor immunity. PD-L1 is abundant in a variety of human cancers (Dong et al (2002) Nat. Med 8:787-9). Expression of PD-L1 on tumors is correlated with reduced survival in esophageal, pancreatic and other types of cancers, highlighting this pathway as a promising target for tumor immunotherapy. Several groups have shown that the PD-1-PD-L1 interaction exacerbates disease, resulting in a decrease in tumor infiltrating lymphocytes, a decrease in T-cell receptor mediated proliferation, and immune evasion by the cancerous cells (Dong et al. (2003) J. Mol. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1.

A single-domain antibody (sdAb) is an antibody consisting of a single monomeric variable antibody domain. Like a whole antibody, it is able to bind selectively to a specific antigen. Single-domain antibodies are much smaller than common antibodies which are composed of two heavy protein chains and two light chains. The first single-domain antibodies were engineered from heavy-chain antibodies found in camelids (Hamers-Casterman C, Atarhouch T, Muyldermans S, Robinson G, Hamers C, Songa E B, Bendahman N, Hamers R (1993) Naturally occurring antibodies devoid of light chains. Nature 363(6428):446-448.); these are called VHH fragments. Currently, most research into single-domain antibodies is based on heavy chain variable domains.

Single-domain antibodies have many advantages. For instance, they generally display high solubility and stability and can also be readily produced in yeast, plant, and mammalian cells (Harmsen M M, De Haard H J (2007) Properties, production, and applications of camelid single-domain antibody fragments. Appl Microbiol Biotechnol 77(1):13-22.). Further, they have good thermal stability and good tissue penetration. And they are also cost efficient in production. The advantages of single-domain antibodies make them suitable for various biotechnological and therapeutic applications. For instance, they are useful in the treatment of diseases, including but not limited to cancer, infectious, inflammatory and neurodegenerative diseases.

Although antibodies against PD-L1 are been developed, there are still spaces for improvement for antibody against PD-L1 as a therapeutic agent. Further, it is worth noting that there are few single-domain antibodies against PD-L1 currently. Accordingly, there is desire in the art to develop anti-PD-L1 antibodies, particularly single-domain antibodies against PD-L1.

SUMMARY OF THE INVENTION

These and other objectives are provided for by the present disclosure which, in a broad sense, is directed to compounds, methods, compositions and articles of manufacture that provide antibodies with improved efficacy. The benefits provided by the present disclosure are broadly applicable in the field of antibody therapeutics and diagnostics and may be used in conjunction with antibodies that react with a variety of targets. The present disclosure provides anti-PD-L1 antibodies, preferably single-domain antibodies. It also provides methods of preparing the antibodies, nucleic acid molecules encoding the anti-PD-L1 antibodies, expression vectors and host cells used for the expression of anti-PD-L1 antibodies. The antibodies of the disclosure provide methods for treating or preventing conditions associated with PD-L1.

In some aspects, the disclosure is directed to a PD-L1 binding molecule.

In some embodiments, the PD-L1 binding molecule has one or more of the following properties:

(a) it binds human PD-L1 with a $K_D$ of $1 \times 10^{-9}$ M or less;

(b) it inhibits binding of PD-L1 to PD-1;

(c) it induces production of IFN-$\gamma$ or IL-2 in CD4+ T cells;

(d) it does not substantially bind to human PD-L2, CD80 and CD86;

(e) it has cross-reactivity with human, mouse or cynomolgus PD-L1; and (f) it is stable at least at 60° C.

In some embodiments, the PD-L1 binding molecule comprises at least one immunoglobulin single variable domain (for example, VHH), wherein the VHH comprises CDR1, CDR2 and CDR3, and wherein CDR1 comprises an amino acid sequence as set forth in SEQ ID NO: 1, CDR2 comprises an amino acid sequence as set forth in SEQ ID NO: 2, and CDR3 comprises an amino acid sequence as set forth in SEQ ID NO: 3.

In some embodiments, the PD-L1 binding molecule comprises at least one immunoglobulin single variable domain (for example, VHH), wherein the VHH comprises CDR1, CDR2 and CDR3, and wherein CDR1 consists of an amino acid sequence as set forth in SEQ ID NO: 1, CDR2 consists of an amino acid sequence as set forth in SEQ ID NO: 2, and CDR3 consists of an amino acid sequence as set forth in SEQ ID NO: 3.

In some embodiments, the PD-L1 binding molecule comprises at least one immunoglobulin single variable domain (for example, VHH), wherein the VHH comprises (A) the amino acid sequence as set forth in SEQ ID NO: 4;

(B) an amino acid sequence which is at least 85%, at least 90%, or at least 95% identical to SEQ ID NO: 4; or (C) an amino acid sequence with addition, deletion and/or substitution of one or more (for example, 1, 2, 3, 4, 5, 6, 7, 8, 9 or 10) amino acids compared with SEQ ID NO: 4.

In some embodiments, the PD-L1 binding molecule is a PD-1 antagonist, for example, an anti-PD-L1 antibody.

In some embodiments, the PD-L1 binding molecule is a single-domain antibody, for example a heavy chain single-domain antibody.

In some embodiments, the PD-L1 binding molecule is a chimeric antibody or a humanized antibody.

In some embodiments, the VHH is from a camelid animal, comprising an alpaca or a llama.

In some embodiments, the VHH is fused to another molecule, comprising a Fc domain of an immunoglobin, a fluorescent protein, or a VHH with a distinct specificity.

In some embodiments, the VHH is fused to a Fc domain of IgG. In further embodiments, the PD-L1 binding molecule is a chimeric antibody of VHH from a camelid animal and Fc domain of human IgG. In further embodiments, the PD-L1 binding molecule is a chimeric antibody of VHH from a camelid animal and Fc domain of human IgG1 or IgG4.

In some embodiments, the PD-L1 binding molecule as disclosed herein is used in inhibiting or blocking the binding of PD-L1 to PD-1.

In some embodiments, the PD-L1 binding molecule as disclosed herein is used in treating or preventing a condition associated with PD-L1 in a subject.

In some aspects, the disclosure is directed to a PD-L1 binding molecule which competes for the same epitope with the PD-L1 binding molecule as disclosed herein.

In some aspects, the disclosure is directed to an isolated nucleic acid molecule, comprising a nucleic acid sequence encoding PD-L1 binding molecule as disclosed herein.

In some embodiments, the isolated nucleic acid molecule comprises or consists of a nucleic acid sequence as set forth in SEQ ID NO: 5.

In some aspects, the disclosure is directed to an expression vector comprising the nucleic acid molecule encoding the PD-L1 binding molecule as disclosed herein.

In some aspects, the disclosure is directed to a host cell comprising the expression vector as disclosed herein.

In some embodiments, the host cell is selected from, but not limited to, a bacterial cell (for example, *E. coli*), fungal cell (for example, a yeast) or a mammalian cell.

In some aspects, the disclosure is directed to a pharmaceutical composition comprising at least one PD-L1 binding molecule as disclosed herein and a pharmaceutically acceptable carrier.

In some aspects, the disclosure is directed to a method for preparing the PD-L1 binding molecule which comprises culturing the host cell comprising the expression vector as defined above under a condition of expressing the PD-L1 binding molecule in the host cell and isolating the PD-L1 binding molecule from the host cell.

In some aspects, the disclosure is directed to a method for inhibiting or blocking the binding of PD-L1 to PD-1 in a subject, comprising: administering a therapeutically effective amount of the PD-L1 binding molecule as disclosed herein to the subject.

In some aspects, the disclosure is directed to a method of treating a condition associated with PD-L1 in a subject, comprising: administering a therapeutically effective amount of the PD-L1 binding molecule as disclosed herein to the subject.

In some embodiments, the subject has been identified as having a disorder or a condition likely to respond to a PD-L1 antagonist.

In some aspects, the disclosure is directed to a method of treating a condition in a subject that would benefit from upregulation of immune response, comprising administering a therapeutically effective amount of the PD-L1 binding molecule as disclosed herein to the subject.

In some embodiments, the subject has upregulated expression of PD-L1.

In some aspects, the disclosure is directed to the use of the PD-L1 binding molecule as disclosed herein in the manufacture of a medicament for treating or preventing proliferative disorders such as cancers.

In some aspects, the disclosure is directed to the use of PD-L1 binding molecule as disclosed herein in the manufacture of a medicament for treating or preventing a condition that would benefit from upregulation of immune response.

In some embodiments, the condition is a proliferative disorder comprising cancer, or an infection.

In some embodiments, the cancer is selected from the group consisting of: breast, lung, colon, ovarian, melanoma, bladder, kidney, liver, salivary, stomach, gliomas, thyroid, thymic, epithelial, head and neck cancers, gastric and pancreatic cancer.

In some embodiments, the infection is a chronic infection.

In some aspects, the disclosure is directed to kits or devices and associated methods that employ the PD-L1 binding molecule as disclosed herein, and pharmaceutical compositions as disclosed herein, which are useful for the treatment of proliferative disorders such as cancer. To this end, the present disclosure preferably provides an article of manufacture useful for treating such disorders comprising a receptacle containing the PD-L1 binding molecule as disclosed herein and instructional materials for using the PD-L1 binding molecule as disclosed herein to treat, ameliorate or prevent a proliferative disorder or progression or recurrence thereof. In selected embodiments, the devices and associated methods will comprise the step of contacting at least one circulating tumor cell with the PD-L1 binding molecule as disclosed herein.

The foregoing is a summary and thus contains, by necessity, simplifications, generalizations, and omissions of detail; consequently, those skilled in the art will appreciate that the summary is illustrative only and is not intended to be in any way limiting. Other aspects, features, and advantages of the methods, compositions and/or devices and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter. Further, the contents of all references, patents and published patent applications cited throughout this application are incorporated herein in entirety by reference.

BRIEF DESCRIPTION OF THE FIGURES

FIG. 1 shows the binding of anti-PD-L1 antibodies to cell surface PD-L1, expressed by MFI (Median Fluorescence Intensity) and measured by FACS. FIG. 1A shows the binding of anti-PD-L1 antibodies to cell surface human PD-L1. FIG. 1B shows the binding of anti-PD-L1 antibodies to cell surface mouse PD-L1. FIG. 1C shows the binding of anti-PD-L1 antibodies to cell surface monkey PD-L1.

FIG. 2 shows the blockage on the binding of PD-1 to cell surface PD-L1 or CD80 by anti-PD-L1 antibodies, as measured by FACS.

FIG. 2C shows the blockage on the binding of human PD-L1 to cell surface human CD80 by anti-PD-L1 antibodies.

FIG. 3 shows cross-reactivity to human PD-1, PD-L2, CD80 and CD86 as measured by ELISA.

FIG. 5 shows the effects of anti-PD-L1 antibodies on human allogeneic mixed lymphocyte reaction (Allo-MLR) or autologous MLR, as measured by ELISA and reflected by the level of IL-2 (pg/mL) or IFN-$\gamma$ (ng/ml). FIG. 5A shows the effects of anti-PD-L1 antibodies on human Allo-MLR, as reflected by the level of human IL-2 (hIL-2). FIG. 5B shows the effects of anti-PD-L1 antibodies on human Allo-MLR, as reflected by the level of human IFN-$\gamma$ (hIFN-$\gamma$). FIG. 5C shows the effects of anti-PD-L1 antibodies on human autologous MLR, as reflected by the level of human IFN-$\gamma$ (hIFN-$\gamma$).

FIG. 6 shows the effects of anti-PD-L1 antibodies on mouse allogeneic MLR, as measured by ELISA and reflected by the level of IL-2 (pg/mL) or counts per minute (CPM).

FIG. 6A shows the effects of anti-PD-L1 antibodies on mouse allogeneic MLR, as reflected by the level of mouse IL-2 (mIL-2). FIG. 6B shows the effects of anti-PD-L1 antibodies on mouse allogeneic MLR, as reflected by the level of CPM.

DETAILED DESCRIPTION OF THE INVENTION

Figure 2A:
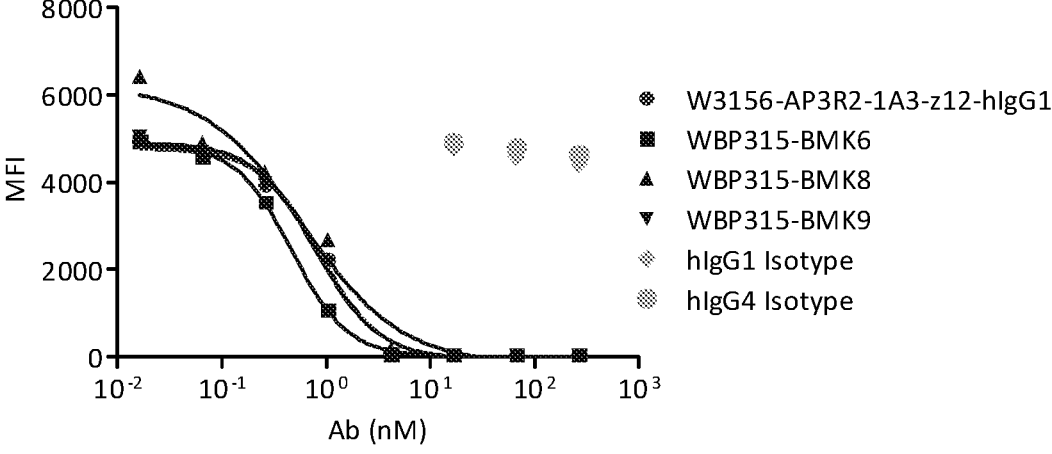
FIG. 2A shows the blockage on the binding of human PD-1 to cell surface human PD-L1 by anti-PD-L1 antibodies.

While the present disclosure may be embodied in many different forms, disclosed herein are specific illustrative embodiments thereof that exemplify the principles of the disclosure. It should be emphasized that the present disclosure is not limited to the specific embodiments illustrated. Moreover, any section headings used herein are for organizational purposes only and are not to be construed as limiting the subject matter described.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. More specifically, as used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like. In this application, the use of "or" means "and/or" unless stated otherwise. Furthermore, the use of the term "comprising," as well as other forms, such as "comprises" and "comprised", is not limiting. In addition, ranges provided in the specification and appended claims include both end points and all points between the end points.

Generally, nomenclature used in connection with, and techniques of, cell and tissue culture, molecular biology, immunology, microbiology, genetics and protein and nucleic acid chemistry and hybridization described herein are well known and commonly used in the art. The methods and techniques of the present disclosure are generally performed according to conventional methods well known in the art and as described in various general and more specific references that are cited and discussed throughout the present specification unless otherwise indicated. See, e.g., Abbas et al., Cellular and Molecular Immunology, 6$^{th}$ ed., W.B. Saunders Company (2010); Sambrook J. & Russell D. *Molecular Cloning: A Laboratory Manual,* 3rd ed., Cold Spring Harbor Laboratory Press, Cold Spring Harbor, N.Y. (2000); Ausubel et al., *Short Protocols in Molecular Biology: A Compendium of Methods from Current Protocols in Molecular Biology,* Wiley, John & Sons, Inc. (2002); Harlow and Lane *Using Antibodies: A Laboratory Manual,* Cold Spring Harbor Laboratory Press, Cold Spring Harbor, N.Y. (1998); and Coligan et al., *Short Protocols in Protein Science,* Wiley, John & Sons, Inc. (2003). The nomenclature used in connection with, and the laboratory procedures and techniques of, analytical chemistry, synthetic organic chemistry, and medicinal and pharmaceutical chemistry described herein are well known and commonly used in the art. Moreover, any section headings used herein are for organizational purposes only and are not to be construed as limiting the subject matter described.

Definitions

In order to better understand the disclosure, the definitions and explanations of the relevant terms are provided as follows.

The term "antibody" or "Ab", as used herein, generally refers to any form of antibody that exhibits the desired biological or binding activity. It covers, but is not limited to, humanized antibodies, fully human antibodies, chimeric antibodies and single-domain antibodies. An antibody may comprise heavy chain(s) and light chain(s). Heavy chains may be classified into $\mu$, $\delta$, $\gamma$, $\alpha$ and $\varepsilon$, which define isotypes of an antibody as IgM, IgD, IgG, IgA and IgE, respectively. Each heavy chain consists of a heavy chain variable region ($V_H$) and a heavy chain constant region ($C_H$). A heavy chain constant region consists of 3 domains ($C_H1$, $C_H2$ and $C_H3$).

Each light chain consists of a light chain variable region ($V_L$) and a light chain constant region ($C_L$). $V_H$ and $V_L$ region can further be divided into hypervariable regions (called complementary determining regions (CDR)), which are interspaced by relatively conservative regions (called framework region (FR)). Each $V_H$ and $V_L$ consists of 3 CDRs and 4 FRs in the following order: FR1, CDR1, FR2, CDR2, FR3, CDR3, FR4 from N-terminal to C-terminal. Distribution of amino acids in various regions or domains follows the definition in Kabat Sequences of Proteins of Immunological Interest (National Institutes of Health, Bethesda, Md. (1987 and 1991)), or Chothia & Lesk (1987) J. Mol. Biol. 196:901-917; Chothia et al., (1989) Nature 342:878-883. Antibodies may be of different antibody isotypes, for example, IgG (e.g., IgG1, IgG2, IgG3 or IgG4 subtype), IgA1, IgA2, IgD, IgE or IgM antibody.

The term "humanized antibody", as used herein, refers to antibodies in which CDR sequences derived from the germline of another mammalian species, such as a mouse, have been grafted onto human framework sequences. Additional framework region modifications may be made within the human framework sequences.

The term "chimeric antibody", as used herein, refers to antibodies in which the variable region sequences are derived from one species and the constant region sequences are derived from another species, such as an antibody in which the variable region sequences are derived from a mouse antibody and the constant region sequences are derived from a human antibody.

The term "PD-1", as used herein, refers programmed cell death protein, which belongs to the superfamily of immunoglobulin and functions as co-inhibitory receptor to negatively regulate the immune system. PD-1 is a member of the CD28/CTLA-4 family, and has two known ligands including PD-L1 and PD-L2. Alternative names or synonyms for PD-1 include PDCD1, PD1, CD279 and SLEB2, et al. Representative amino acid sequence of human PD-1 is disclosed under the NCBI accession number: NP_005009.2, and the representative nucleic acid sequence encoding the human PD-1 is shown under the NCBI accession number: NM_005018.2.

The term "PD-L1", as used herein, refers to programmed cell death ligand 1 (PD-L1, see, for example, Freeman et al. (2000) J. Exp. Med. 192: 1027). Alternative names or synonyms for PD-L1 include PDCD1L1, PDL1, B7H1, CD274 and B7-H, et al. Representative amino acid sequence of human PD-L1 is disclosed under the NCBI accession number: NP_054862.1 and the representative nucleic acid sequence encoding the human PD-L1 is shown under the NCBI accession number: NM_014143.3. PD-L1 is expressed in placenta, spleen, lymph nodes, thymus, heart, fetal liver, and is also found on many tumor or cancer cells. PD-L1 binds to its receptor PD-1 or B7-1, which is expressed on activated T cells, B cells and myeloid cells. The binding of PD-L1 and its receptor induces signal transduction to suppress TCR-mediated activation of cytokine production and T cell proliferation. Accordingly, PD-L1 plays a major role in suppressing immune system during particular events such as pregnancy, autoimmune diseases, tissue allografts, and is believed to allow tumor or cancer cells to circumvent the immunological checkpoint and evade the immune response.

The term "PD-L2", as used herein, refers to programmed cell death ligand 2. Alternative names or synonyms for PD-L2 include PDCD1L2, PDL2, B7-DC, Btdc and CD273, et al. Representative amino acid sequence of human PD-L2 is disclosed under the NCBI accession number: NP_079515.2.

The term "Anti-PD-L1 antibody", as used herein, refers to an antibody that is capable of specific binding to PD-1 (e.g. human, monkey or monkey PD-1). It is advantage that the Anti-PD-L1 antibody specifically binds to PD-L1 with an affinity which is sufficient to provide for diagnostic and/or therapeutic use.

The term "Ka", as used herein, is intended to refer to the association rate of a particular antibody-antigen interaction, whereas the term "Kd" as used herein, is intended to refer to the dissociation rate of a particular antibody-antigen interaction. Kd values for antibodies can be determined using methods well established in the art. The term "$K_D$" as used herein, is intended to refer to the dissociation constant of a particular antibody-antigen interaction, which is obtained from the ratio of Kd to Ka (i.e., Kd/Ka) and is expressed as a molar concentration (M). A preferred method for determining the Kd of an antibody is by using surface plasmon resonance, preferably using a biosensor system such as a Biacore® system.

The term "specific binding" or "specifically binds" as used herein refers to a non-random binding reaction between two molecules, such as for example between an antibody and an antigen.

The ability to "inhibit binding", "block binding" or "compete for the same epitope", as used herein, refers to the ability of an antibody to inhibit the binding interaction between two molecules (e.g. human PD-L1 and an anti-PD-L1 antibody) to any detectable degree. In some embodiments, an antibody that blocks binding between two molecules inhibits the binding interaction between the two molecules by at least 50%. In some embodiments, this inhibition may be greater than 60%, greater than 70%, greater than 80%, or greater than 90%.

The term "high affinity" for an IgG antibody, as used herein, refers to an antibody having a $K_D$ of $1 \times 10^{-7}$ M or less, more preferably $5 \times 10^{-8}$ M or less, even more preferably $1 \times 10^{-8}$ M or less, even more preferably $5 \times 10^{-9}$ M or less and even more preferably $1 \times 10^{-9}$ M or less for a target antigen.

The term "$EC_{50}$", as used herein, which is also termed as "half maximal effective concentration" refers to the concentration of a drug, antibody or toxicant which induces a response halfway between the baseline and maximum after a specified exposure time. In the context of the application, $EC_{50}$ is expressed in the unit of "nM".

The term "epitope", as used herein, refers to a portion on antigen that an immunoglobulin or antibody specifically binds to. "Epitope" is also known as "antigenic determinant". Epitope or antigenic determinant generally consists of chemically active surface groups of a molecule such as amino acids, carbohydrates or sugar side chains, and generally has a specific three-dimensional structure and a specific charge characteristic. For example, an epitope generally comprises at least 3, 4, 5, 6, 7, 8, 9, 10, 11, 12, 13, 14 or 15 consecutive or non-consecutive amino acids in a unique steric conformation, which may be "linear" or "conformational". See, for example, Epitope Mapping Protocols in Methods in Molecular Biology, Vol. 66, G. E. Morris, Ed. (1996). In a linear epitope, all the interaction sites between a protein and an interaction molecule (e.g., an antibody) are present linearly along the primary amino acid sequence of the protein. In a conformational epitope, the interaction sites span over amino acid residues that are separate from each other in a protein. Antibodies may be screened depending on competitiveness of binding to the same epitope by conventional techniques known by a person skilled in the art. For example, study on competition or cross-competition may be conducted to obtain antibodies that compete or cross-compete with each other for binding to antigens (e.g. RSV fusion protein). High-throughput methods for obtaining antibodies binding to the same epitope, which are based on their cross-competition, are described in an international patent application WO 03/48731.

The term "isolated", as used herein, refers to a state obtained from natural state by artificial means. If a certain "isolated" substance or component is present in nature, it is possible because its natural environment changes, or the substance is isolated from natural environment, or both. For example, a certain un-isolated polynucleotide or polypeptide naturally exists in a certain living animal body, and the same polynucleotide or polypeptide with a high purity isolated from such a natural state is called isolated polynucleotide or polypeptide. The term "isolated" excludes neither the mixed artificial or synthesized substance nor other impure substances that do not affect the activity of the isolated sub stance.

The term "isolated antibody", as used herein, is intended to refer to an antibody that is substantially free of other antibodies having different antigenic specificities (e.g., an isolated antibody that specifically binds a PD-1 protein is substantially free of antibodies that specifically bind antigens other than PD-1 proteins). An isolated antibody that specifically binds a human PD-1 protein may, however, have cross-reactivity to other antigens, such as PD-1 proteins from other species. Moreover, an isolated antibody can be substantially free of other cellular material and/or chemicals.

The term "vector", as used herein, refers to a nucleic acid vehicle which can have a polynucleotide inserted therein. When the vector allows for the expression of the protein encoded by the polynucleotide inserted therein, the vector is called an expression vector. The vector can have the carried genetic material elements expressed in a host cell by transformation, transduction, or transfection into the host cell. Vectors are well known by a person skilled in the art, including, but not limited to plasmids, phages, cosmids, artificial chromosome such as yeast artificial chromosome (YAC), bacterial artificial chromosome (BAC) or P1-derived artificial chromosome (PAC); phage such as λ phage or M13 phage and animal virus. The animal viruses that can be used as vectors, include, but are not limited to, retrovirus (including lentivirus), adenovirus, adeno-associated virus, herpes virus (such as herpes simplex virus), pox virus, baculovirus, papillomavirus, papova virus (such as SV40). A vector may comprise multiple elements for controlling expression, including, but not limited to, a promoter sequence, a transcription initiation sequence, an enhancer sequence, a selection element and a reporter gene. In addition, a vector may comprise origin of replication.

The term "host cell", as used herein, refers to a cell into which a vector can be introduced, including, but not limited to, prokaryotic cell such as E. coli or Bacillus subtilis, fungal cell such as yeast cell or Aspergillus, insect cell such as S2 Drosophila cell or Sf9, and animal cell such as fibroblast, CHO cell, COS cell, NSO cell, HeLa cell, BHK cell, HEK 293 cell or human cell.

CHO cells refer to Chinese Hamster Ovary cells, which include many commercially available subclones, such as CHO-K1, CHO-S, CHO-DXB11, CHO-DG44, etc. Among them, CHO-K1 is generally used as an expression platform. CHO-K1 is commercially available from ATCC, ECACC, DSMZ, and many other companies.

The term "T cell", as used herein, includes CD4+ T cells, CD8+ T cells, T helper 1 type T cells, T helper 2 type T cells, T helper 17 type T cells and inhibitory T cells.

The term "identity", as used herein, refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al, 1988, SIAMJ. Applied Math. 48:1073.

The term "immunogenicity", as used herein, refers to ability of stimulating the formation of specific antibodies or sensitized lymphocytes in organisms. It not only refers to the property of an antigen to stimulate a specific immunocyte to activate, proliferate and differentiate so as to finally generate immunologic effector substance such as antibody and sensitized lymphocyte, but also refers to the specific immune response that antibody or sensitized T lymphocyte can be formed in immune system of an organism after stimulating the organism with an antigen. Immunogenicity is the most important property of an antigen. Whether an antigen can successfully induce the generation of an immune response in a host depends on three factors, properties of an antigen, reactivity of a host, and immunization means.

The term "transfection" or "transfect", as used herein, refers to the process by which nucleic acids are introduced into eukaryotic cells, particularly mammalian cells. Protocols and techniques for transfection include but not limited to lipid transfection and chemical and physical methods such as electroporation. A number of transfection techniques are well known in the art and are disclosed herein. See, e.g., Graham et al., 1973, Virology 52:456; Sambrook et al., 2001, Molecular Cloning: A Laboratory Manual, supra; Davis et al., 1986, Basic Methods in Molecular Biology, Elsevier; Chu et al, 1981, Gene 13:197.

The term "SPR" or "surface plasmon resonance", as used herein, refers to and includes an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 5 and Jonsson, U., et al. (1993) Ann. Biol. Clin. 51:19-26; Jönsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

The term "fluorescence-activated cell sorting" or "FACS", as used herein, refers to a specialized type of flow cytometry. It provides a method for sorting a heterogeneous mixture of biological cells into two or more containers, one cell at a time, based upon the specific light scattering and fluorescent characteristics of each cell (FlowMetric. "Sorting Out Fluorescence Activated Cell Sorting". Retrieved 2017-11-09.). Instruments for carrying out FACS are known to those of skill in the art and are commercially available to the public. Examples of such instruments include FACS Star Plus, FACScan and FACSort instruments from Becton Dickinson (Foster City, Calif.) Epics C from Coulter Epics Division (Hialeah, Fla.) and MoFlo from Cytomation (Colorado Springs, Colo.).

The term "subject" includes any human or nonhuman animal, preferably humans.

The term "condition associated with PD-L1" or "condition related to PD-L1", as used herein, refers to any condition that is caused by, exacerbated by, or otherwise linked to increased or decreased expression or activities of PD-L1 (e.g. a human PD-L1).

The term "cancer", as used herein, refers to any or a tumor or a malignant cell growth, proliferation or metastasis-mediated, solid tumors and non-solid tumors such as leukemia and initiate a medical condition.

The term "treatment", "treating" or "treated", as used herein in the context of treating a condition, pertains generally to treatment and therapy, whether of a human or an animal, in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included. For cancer, "treating" may refer to dampen or slow the tumor or malignant cell growth, proliferation, or metastasis, or some combination thereof. For tumors, "treatment" includes removal of all or part of the tumor, inhibiting or slowing tumor growth and metastasis, preventing or delaying the development of a tumor, or some combination thereof.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen. Specifically, the "therapeutically-effective amount," refers to an antibody in an amount or concentration effective to treat the human PD-1-related diseases or conditions.

The present disclosure in a "host cell", as used herein, refers to a cell with the introduction of exogenous polynucleotides.

The term "therapeutically effective amount" or "effective amount", as used herein, refers to a drug in an amount or concentration effective to treat the human PD-1-related diseases or conditions.

The term "pharmaceutically acceptable", as used herein, means that the vehicle, diluent, excipient and/or salts thereof, are chemically and/or physically is compatible with other ingredients in the formulation, and the physiologically compatible with the recipient.

As used herein, the term "a pharmaceutically acceptable carrier and/or excipient" refers to a carrier and/or excipient pharmacologically and/or physiologically compatible with a subject and an active agent, which is well known in the art (see, e.g., Remington's Pharmaceutical Sciences. Edited by Gennaro AR, 19th ed. Pennsylvania: Mack Publishing Company, 1995), and includes, but is not limited to pH adjuster, surfactant, adjuvant and ionic strength enhancer. For example, the pH adjuster includes, but is not limited to, phosphate buffer; the surfactant includes, but is not limited to, cationic, anionic, or non-ionic surfactant, e.g., Tween-80; the ionic strength enhancer includes, but is not limited to, sodium chloride.

As used herein, the term "adjuvant" refers to a non-specific immunopotentiator, which can enhance immune response to an antigen or change the type of immune response in an organism when it is delivered together with the antigen to the organism or is delivered to the organism in advance. There are a variety of adjuvants, including, but not limited to, aluminium adjuvants (for example, aluminum hydroxide), Freund's adjuvants (for example, Freund's complete adjuvant and Freund's incomplete adjuvant), coryne bacterium parvum, lipopolysaccharide, cytokines, and the like. Freund's adjuvant is the most commonly used adjuvant in animal experiments now. Aluminum hydroxide adjuvant is more commonly used in clinical trials.

PD-L1 Binding Molecules

In some aspects, the disclosure comprises PD-L1 binding molecule.

The PD-L1 binding molecule, in a general sense, may include any molecule that specifically binds to PD-L1. In some circumstances, "PD-L1 binding molecule" may include "PD-L1 antagonist". "PD-L1 antagonist" refers to any chemical compound or biological molecule that blocks the binding of PD-L1 to PD-1 expressed on an immune cell (T cell, B cell or NKT cell). The PD-L1 binding molecule or PD-1 antagonist may be a polypeptide or a protein, for example, an antibody, more particularly, an anti-PD-L1 antibody.

The antibody includes, but not limited to, a chimeric antibody, a humanized antibody, or a single-domain antibody. In a specific embodiment, the PD-L1 binding molecule is a single-domain antibody, which generally refers to an antibody consisting of a single monomeric variable antibody domain. Like a whole antibody, a single-domain antibody is able to bind selectively to a specific antigen.

More specifically, the PD-L1 binding molecule is a single-domain heavy chain antibody, which is interchangeably used with the terms "VHH", "VHH antibody", "VHH domain", "VHH antibody fragment", "$V_{HH}$" or "Nanobody," et al. $V_{HH}$ molecules derived from Camelidae antibodies are among the smallest intact antigen-binding domains known (approximately 15 kDa, or 10 times smaller than a conventional IgG) and hence are well suited towards delivery to dense tissues and for accessing the limited space between macromolecules.

The single-domain antibody of the disclosure disclosed herein may be made by the skilled artisan according to methods known in the art or any future method. For example, VHHs may be obtained using methods known in the art such as by immunizing a camel and obtaining hybridoma's therefrom, or by cloning a library of VHHs of the disclosure using molecular biology techniques known in the art and subsequent selection by using phage display.

For instance, a single-domain antibody can be obtained by immunization of llamas or alpacas with the desired antigen and subsequent isolation of the mRNA coding for heavy-chain antibodies. By reverse transcription and polymerase chain reaction, a gene library of single-domain antibodies containing several million clones is produced. Screening techniques like phage display and ribosome display help to identify the clones binding the antigen. One technique is phage display in which a library of (e.g., human) antibodies is synthesized on phages, the library is screened with the antigen of interest or an antibody-binding portion thereof, and the phage that binds the antigen is isolated, from which one may obtain the immunoreactive fragments. Methods for preparing and screening such libraries are well known in the art and kits for generating phage display libraries are commercially available (e.g., the Pharmacia Recombinant Phage Antibody System, catalog no. 27-9400-01; and the Stratagene SurfZAP phage display kit, catalog no. 240612). There also are other methods and reagents that can be used in generating and screening antibody display libraries (see, e.g., Barbas et al., Proc. Natl. Acad. Sci. USA 88:7978-7982 (1991)).

When the most potent clones have been identified, their DNA sequence is optimized, for example, by affinity maturation or humanization. Humanization may prevent immunological reactions of the human organism against the antibody.

Accordingly, the single-domain antibodies can be obtained (1) by isolating the VHH domain of a naturally occurring heavy chain antibody; (2) by expression of a nucleotide sequence encoding a naturally occurring VHH domain; (3) by "humanization" (as described below) of a naturally occurring VHH domain or by expression of a nucleic acid encoding a such humanized VHH domain; (4) by "camelization" of a naturally occurring VH domain from any animal species, in particular a species of mammal, such as from a human being, or by expression of a nucleic acid encoding such a camelized VH domain; (5) by "camelisation" of a "domain antibody" or "Dab" as described by Ward et al (supra), or by expression of a nucleic acid encoding such a camelized VH domain; (6) using synthetic or semi-synthetic techniques for preparing proteins, polypeptides or other amino acid sequences; (7) by preparing a nucleic acid encoding a VHH using techniques for nucleic acid synthesis, followed by expression of the nucleic acid thus obtained; and/or (8) by any combination of the foregoing. Suitable methods and techniques for performing the foregoing will be clear to the skilled person based on the disclosure herein and for example include the methods and techniques described in more detail hereinbelow.

Single-domain antibodies are usually generated by PCR cloning of variable domain repertoire from blood, lymph node, or spleen cDNA obtained from immunized animals into a phage display vector. Antigen-specific single-domain antibodies are commonly selected by panning phase libraries on immobilized antigen, e.g., antigen coated onto the plastic surface of a test tube, biotinylated antigens immobilized on Streptavidin beads, or membrane proteins expressed on the surface of cells. The affinity of adAbs can often been improved by mimicking this strategy in vitro, for instance, by site directed mutagenesis of the CDR regions and further rounds of panning on immobilized antigen under conditions of increased stringency (higher temperature, high or low salt concentration, high or low pH, and low antigen concentrations) (Wesolowski et al., Single domain antibodies: promising experimental and therapeutic tools in infection and immunity. Med Microbiol Immunol (2009) 198: 157-174).

Methods for preparing a VHH specifically binding to an antigen or epitope was described in references, for example: R. van der Linden et al., Journal of Immunological Methods, 240(2000) 185-195; Li et al., J Biol Chem., 287(2012) 13713-13721; Deffar et al., African Journal of Biotechnology Vol. 8(12), pp. 2645, 17 Jun., 2009 and WO94/04678.

In some embodiments, the VHH in the PD-L1 binding molecule is fused to an Fc-domain of an antibody, for example, Fc-domain of IgG (e.g., IgG4 or IgG1). In a specific embodiment, the Fc-domain is an Fc-domain of human IgG1. By fusing a VHH to a Fc domain, it may be more efficient to recruit effector functions. Also, the fusion of VHH to Fc domain may help the PD-L1 binding molecule to form a dimer, and may also help the extension of the half life of PD-L1 binding molecule in vivo.

The term "antibody-dependent cell-mediated cytotoxicity" or "ADCC", as used herein, refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA) 95:652-656 (1998).

The term "complement dependent cytotoxicity" or "CDC" refers to the lysis of a target cell in the presence of complement. Activation of the classical complement pathway is initiated by the binding of the first component of the complement system (Clq) to antibodies (of the appropriate subclass) which are bound to their cognate antigen. To assess complement activation, a CDC assay, e.g. as described in Gazzano-Santoro et al., J. Immunol. Methods 202: 163 (1996), may be performed.

For convenience of description, the PD-L1 binding molecule is described as anti-PD-L1 antibody in the following sections.

Anti-PD-L1 Antibodies with Certain Properties

The antibody of the disclosure is characterized by particular functional features or properties of the antibodies. In some embodiments, the antibody has one or more of the following properties:

(a) it binds human PD-L1 with a $K_D$ of $1 \times 10^{-9}$ M or less;

(b) it inhibits binding of PD-L1 to PD-1;

(c) it induces production of IFN-γ or IL-2 in CD4+ T cells;

(d) it does not substantially bind to human PD-L2, CD80 and CD86;

(e) it has cross-reactivity with human, mouse or cynomolgus PD-L1; and (f) it is stable at least at 60° C.

The antibody of the disclosure binds to cell surface PD-L1 with high affinity. The binding of an antibody of the disclosure to PD-L1 can be assessed using one or more techniques well established in the art, for instance, ELISA. The binding specificity of an antibody of the disclosure can also be determined by monitoring binding of the antibody to cells expressing a PD-L1 protein, e.g., flow cytometry. For example, an antibody can be tested by a flow cytometry assay in which the antibody is reacted with a cell line that expresses human PD-L1, such as CHO cells that have been transfected to express PD-L1 on their cell surface. Additionally or alternatively, the binding of the antibody, including the binding kinetics (e.g., Kd value) can be tested in BIAcore binding assays. Still other suitable binding assays include ELISA assays, for example using a recombinant PD-L1 protein. For instance, an antibody of the disclosure binds to a cell surface (e.g., human PD-L1) protein with a $K_D$ of $1 \times 10^{-7}$ M or less, $5 \times 10^{-8}$ M or less, $2 \times 10^{-8}$ M or less,

15

$5\times10^{-9}$ M or less, $4\times10^{-9}$ M or less, $3\times10^{-9}$ M or less, $2\times10^{-9}$ M or less, $1\times10^{-9}$ M or less, $5\times10^{10}$ M or less, $1\times10^{-1\circ}$ M or less.

In some embodiments, the antibodies of the disclosure bind to cynomolgus or monkey PD-L1 at an $EC_{50}$ of no more than or about 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 0.09 nM, 0.08 nM, 0.07 nM, 0.06 nM, 0.05 nM, 0.04 nM, 0.03 nM, 0.02 nM, or 0.01 nM, as measured by FACS.

In some embodiments, the antibodies of the disclosure inhibit the binding of human PD-1 to PD-L1 at an $IC_{50}$ of 0.2 nM to 100 nM (e.g. 0.2 nM to 50 nM, 0.2 nM to 30 nM, 0.2 nM to 20 nM, 0.2 nM to 10 nM, or 1 nM to 10 nM), as measured by, for instance, ELISA.

The anti-PD-L1 antibodies of the disclosure are specific for PD-L1. In some embodiments, the antibodies do not bind to PD-L2, CD80 and/or CD86. For example, the binding affinity with PD-L2, CD80 and/or CD86 is less than 15%, 10%, 9%, 8%, 7%, 6%, 5%, 4%, 3%, 2%, or 1% of the binding affinity with PD-L1.

In some embodiments, the antibodies of the disclosure block binding of human PD-L1 to PD-1 and thereby providing biological activity including, for example, inducing cytokine production from the activated T cells (such as CD4+ T cells and CD8+ T cells), inducing proliferation of activated T cells (such as CD4+ T cells and CD8+ T cells), and reversing T reg's suppressive function. Exemplary cytokines include IL-2 and IFNγ. The term "IL-2" refers to interleukin 2, a type of cytokine signaling molecule in the immune system that regulates the activities of white blood cells (e.g. leukocytes). The term "Interferon gamma (IFNγ)" is a cytokine that is produced by natural killer (NK), NK T cells, CD4+ and CD8+ T cells, which is a critical activator of macrophages and inducer of major histocompatibility complex (MHC) molecule expression. The cytokine production can be determined using methods known in the art, for example, by ELISA. Methods can also be used to detect proliferation of T cells, including [3H] thymidine incorporation assay.

Anti-PD-L1 Antibodies Comprising CDRs

In some embodiments, the anti-PD-L1 antibody as disclosed herein comprises at least one immunoglobulin single variable domain (for example, VHH), wherein the VHH comprises CDR1, CDR2 and CDR3, and wherein CDR1 comprises an amino acid sequence as set forth in SEQ ID NO: 1, CDR2 comprises an amino acid sequence as set forth in SEQ ID NO: 2, and CDR3 comprises an amino acid sequence as set forth in SEQ ID NO: 3.

The assignment of amino acids to each CDR may be in accordance with one of the numbering schemes provided by Kabat et al. (1991) *Sequences of Proteins of Immunological Interest* ($5^{th}$ Ed.), US Dept. of Health and Human Services, PHS, NIH, NIH Publication no. 91-3242; Chothia et al., 1987, PMID: 3681981; Chothia et al., 1989, PMID: 2687698; MacCallum et al., 1996, PMID: 8876650; or Dubel, Ed. (2007) *Handbook of Therapeutic Antibodies, $3^{rd}$* Ed., Wily-VCH Verlag GmbH and Co. unless otherwise noted.

Variable regions and CDRs in an antibody sequence can be identified according to general rules that have been developed in the art (as set out above, such as, for example, the Kabat numbering system) or by aligning the sequences against a database of known variable regions. Methods for identifying these regions are described in Kontermann and Dubel, eds., Antibody Engineering, Springer, New York, N.Y., 2001 and Dinarello et al., Current Protocols in Immunology, John Wiley and Sons Inc., Hoboken, N.J., 2000. Exemplary databases of antibody sequences are described in, and can be accessed through, the "Abysis" website at www.bioinf.org.uk/abs (maintained by A.C. Martin in the Department of Biochemistry & Molecular Biology University College London, London, England) and the VBASE2 website at www.vbase2.org, as described in Retter et al., Nucl. Acids Res., 33 (Database issue): D671-D674 (2005). Preferably sequences are analyzed using the Abysis database, which integrates sequence data from Kabat, IMGT and the Protein Data Bank (PDB) with structural data from the PDB. See Dr. Andrew C. R. Martin's book chapter Protein Sequence and Structure Analysis of Antibody Variable Domains. In: Antibody Engineering Lab Manual (Ed.: Duebel, S. and Kontermann, R., Springer-Verlag, Heidelberg, ISBN-13: 978-3540413547, also available on the website bioinforg.uk/abs). The Abysis database website further includes general rules that have been developed for identifying CDRs which can be used in accordance with the teachings herein.

Unless otherwise indicated, all CDRs set forth herein are derived according to the Abysis database website as per Kabat.

In some embodiments, the anti-PD-L1 antibody as disclosed herein comprises at least one immunoglobulin single variable domain (for example, VHH), wherein the VHH comprises CDR1, CDR2 and CDR3, and wherein CDR1 is consisted of an amino acid sequence as set forth in SEQ ID NO: 1, CDR2 is consisted of an amino acid sequence as set forth in SEQ ID NO: 2, and CDR3 is consisted of an amino acid sequence as set forth in SEQ ID NO: 3.

In a specific embodiment, the anti-PD-L1 antibody as disclosed herein comprises one VHH, wherein the VHH comprises CDR1, CDR2 and CDR3, and wherein CDR1 is consisted of an amino acid sequence as set forth in SEQ ID NO: 1, CDR2 is consisted of an amino acid sequence as set forth in SEQ ID NO: 2, and CDR3 is consisted of an amino acid sequence as set forth in SEQ ID NO: 3.

Anti-PD-L1 Antibodies Defined Via the Sequence of VHH

In some embodiments, the anti-PD-L1 antibodies comprises at least one immunoglobulin single variable domain (for example, VHH), wherein the VHH comprises or consists of:

(A) the amino acid sequence as set forth in SEQ ID NO: 4;

(B) an amino acid sequence which is at least 85%, at least 90%, or at least 95% identical to SEQ ID NO: 4; or (C) an amino acid sequence with addition, deletion and/or substitution of one or more (for example, 1, 2, 3, 4, 5, 6, 7, 8, 9 or 10) amino acids compared with SEQ ID NO: 4.

The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present disclosure can further be used as a "query sequence" to perform a search against public databases to, for example, identify related sequences. Such searches can be performed using the XBLAST program (version 2.0) of Altschul, et al. (1990) J. Mol. Biol. 215:403-10. BLAST protein searches can be performed with the XBLAST program, score=50, wordlength=3 to obtain amino acid sequences homologous to the antibody molecules of the disclosure. To obtain gapped alignments for comparison purposes, Gapped BLAST can be utilized as described in Altschul et al, (1997) Nucleic Acids Res. 25(17):3389-3402. When utilizing BLAST and Gapped BLAST programs, the default parameters of the respective programs (e.g., XBLAST and NBLAST) can be used. See www.ncbi.nlm.nih.gov.

In some embodiments, the amino acid sequences of VHH can be at least 85%, 86%, 87%, 88%, 89%, 90%, 91%, 92%, 93%, 94%, 95%, 96%, 97%, 98% or 99% identical to SEQ ID NO: 4.

In some further embodiments, the anti-PD-L1 antibodies may contain conservative substitution or modification of amino acids in the variable regions of the heavy chain and/or light chain. It is understood in the art that certain conservative sequence modification can be made which do not remove antigen binding. See, e.g., Brummell et al. (1993) Biochem 32:1180-8; de Wildt et al. (1997) Prot. Eng. 10:835-41; Komissarov et al. (1997) J. Biol. Chem. 272: 26864-26870; Hall et al. (1992) J. Immunol. 149:1605-12; Kelley and O' Connell (1993) Biochem. 32:6862-35; Adib-Conquy et al. (1998) Int. Immunol. 10:341-6 and Beers et al. (2000) Clin. Can. Res. 6:2835-43.

As described above, the term "conservative substitution", as used herein, refers to amino acid substitutions which would not disadvantageously affect or change the essential properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having alkaline side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having (3-branched side chains (such as threonine, valine, isoleucine) and amino acids having aromatic side chains (for example, tyrosine, phenylalanine, tryptophan, histidine). Therefore, a corresponding amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997), which are incorporated herein by reference).

In some specific embodiments, the anti-PD-L1 antibody comprises one VHH, and the VHH is consisted of the amino acid sequence as set forth in SEQ ID NO: 4. In one embodiment, the anti-PD-L1 antibody is consisted of one VHH which is consisted of the amino acid sequence as set forth in SEQ ID NO: 4, and this antibody is named as "AP3R2-1A3-z12-Ig4" in the context of the disclosure.

In some other specific embodiments, the anti-PD-L1 antibody is a chimeric antibody, comprising one VHH fused to a Fc domain of human IgG1 or IgG4. In one embodiment, the anti-PD-L1 antibody is a chimeric antibody consisted of one VHH and a Fc domain of human IgG1, which is named as "AP3R2-1A3-z12-hIgG1" in the context of the disclosure.

Binning and Epitope Mapping

It will further be appreciated the disclosed antibodies will associate with, or bind to, discrete epitopes or immunogenic determinants presented by the selected target or fragment thereof. In some embodiments, epitope or immunogenic determinants include chemically active surface groupings of molecules such as amino acids, sugar side chains, phosphoryl groups, or sulfonyl groups. In some embodiments, epitopes may have specific three-dimensional structural characteristics, and/or specific charge characteristics. Thus, as used herein the term "epitope" includes any protein determinant capable of specific binding to an immunoglobulin or T-cell receptor or otherwise interacting with a molecule. In some embodiments, an antibody is said to specifically bind (or immune-specifically bind or react) an antigen when it preferentially recognizes its target antigen in a complex mixture of proteins and/or macromolecules. In some embodiments, an antibody is said to specifically bind an antigen when the equilibrium dissociation constant ($K_D$) is less than or equal to $10^{-6}$ M or less than or equal to $10^{-7}$ M, more preferably when the e $K_D$ is less than or equal to $10^{-8}$ M, and even more preferably when the $K_D$ is less than or equal to $10^9$ M.

Epitopes formed from contiguous amino acids (sometimes referred to as "linear" or "continuous" epitopes) are typically retained upon protein denaturing, whereas epitopes formed by tertiary folding are typically lost upon protein denaturing. In any event an antibody epitope typically includes at least 3, and more usually, at least 5 or 8-10 amino acids in a unique spatial conformation.

In this respect, it will be appreciated that, in some embodiments, an epitope may be associated with, or reside in, one or more regions, domains or motifs of, for example, the anti-PD-L1 antibody. Similarly, the art-recognized term "motif" will be used in accordance with its common meaning and shall generally refer to a short, conserved region of a protein that is typically ten to twenty contiguous amino acid residues.

In any event once a desired epitope on an antigen is determined, it is possible to generate antibodies to that epitope, e.g., by immunizing with a peptide comprising the epitope using techniques described in the present disclosure. Alternatively, during the discovery process, the generation and characterization of antibodies may elucidate information about desirable epitopes located in specific domains or motifs. From this information, it is then possible to competitively screen antibodies for binding to the same epitope. An approach to achieve this is to conduct competition studies to find antibodies that competitively bind with one another, i.e. the antibodies compete for binding to the antigen. A high throughput process for binning antibodies based upon their cross-competition is described in WO 03/48731. Other methods of binning or domain level or epitope mapping comprising antibody competition or antigen fragment expression on yeast are well known in the art.

As used herein, the term "binning" refers to methods used to group or classify antibodies based on their antigen binding characteristics and competition. While the techniques are useful for defining and categorizing the antibodies of the instant disclosure, the bins do not always directly correlate with epitopes and such initial determinations of epitope binding may be further refined and confirmed by other art-recognized methodology in the art and as described herein. However, it will be appreciated that empirical assignment of the antibodies to individual bins provides information that may be indicative of the therapeutic potential of the disclosed antibodies.

More specifically, one can determine whether a selected reference antibody (or fragment thereof) binds to the same epitope or cross competes for binding with a second test antibody (i.e., is in the same bin) by using methods known in the art and set forth in the Examples herein.

Other compatible epitope mapping techniques include alanine scanning mutants, peptide blots (Reineke (2004) Methods Mol Biol 248:443-63) (herein specifically incorporated by reference in its entirety), or peptide cleavage analysis. In addition, methods such as epitope excision, epitope extraction and chemical modification of antigens can be employed (Tomer (2000) Protein Science 9: 487-496) (herein specifically incorporated by reference in its entirety). Nucleic Acid Molecules Encoding Antibodies of the Invention In some aspects, the disclosure is directed to an isolated nucleic acid molecule, comprising a nucleic acid sequence encoding VHHs as disclosed herein.

Nucleic acids of the disclosure can be obtained using standard molecular biology techniques. For antibodies obtained from an immunoglobulin gene library (e.g., using phage display techniques), a nucleic acid encoding such antibodies can be recovered from the gene library.

Exemplary nucleic acid molecule of the disclosure is the one set forth SEQ ID No: 5. In some embodiments, the nucleic acids share an at least 80% (e.g. at least 85%, 86%, 87%, 88%, 89%, 90%, 91%, 92%, 93%, 94%, 95%, 96%, 97%, 98%, or 99%) sequence identity to SEQ ID NO: 5. In some embodiments, the percentage of identity is derived from the degeneracy of the genetic code, and the encoded protein sequences remain unchanged.

The nucleic acid molecules that encodes the anti-PD-L1 antibodies can be inserted into a vector for further cloning (amplification of the DNA) or for expression, using recombinant techniques known in the art. In another embodiment, the antibody may be produced by homologous recombination known in the art. DNA encoding the monoclonal antibody is readily isolated and sequenced using conventional procedures (e.g., by using oligonucleotide probes that are capable of binding specifically to genes encoding the heavy chain of the antibody). Many vectors are available. The vector components generally include, but are not limited to, one or more of the following: a signal sequence, an origin of replication, one or more marker genes, an enhancer element, a promoter (e.g. SV40, CMV, EF-1α), and a transcription termination sequence. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Selectable marker genes may include the dihydrofolate reductase (DHFR) gene (for use in dhfr-host cells with methotrexate selection/amplification) and the neo gene (for G418 selection).

In some embodiments, the vector system includes mammalian, bacterial, yeast systems, etc, and comprises plasmids such as, but not limited to, pALTER, pBAD, pcDNA, pCal, pL, pET, pGEMEX, pGEX, pCI, pCMV, pEGFP, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS420, pLexA, pACT2.2 etc, and other laboratorial and commercially available vectors. Suitable vectors may include, plasmid, or viral vectors (e.g., replication defective retroviruses, adenoviruses and adeno-associated viruses). In one embodiment of the disclosure, the vector may be pET, for instance, pETbac containing genes of hexa-histidine- and c-Myc-tag.

Vectors comprising the nucleic acid sequence encoding the PD-L1 binding molecule can be introduced to a host cell for cloning or gene expression. Suitable host cells for cloning or expressing the DNA in the vectors herein are the prokaryote, yeast, or higher eukaryote cells. Suitable prokaryotes for this purpose include eubacteria, such as Gram-negative or Gram-positive organisms, for example, Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*.

In addition to prokaryotes, eukaryotic microbes such as filamentous fungi or yeast are suitable cloning or expression hosts for anti-PD-L1 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Other suitable host cells for the expression of the anti-PD-L1 antibodies provided here are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present disclosure, particularly for transfection of *Spodoptera frugiperda* cells. Plant cell cultures of cotton, corn, potato, soybean, *petunia*, tomato, and tobacco can also be utilized as hosts.

Host cells are transformed with the above-described expression or cloning vectors for anti-PD-L1 antibody production and cultured in conventional nutrient media modified as appropriate for inducing promoters, selecting transformants, or amplifying the genes encoding the desired sequences.

The host cells used to produce the anti-PD-L1 antibodies provided herein may be cultured in a variety of media. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the host cells. In addition, any of the media described in Ham et al., Meth. Enz. 58: 44 (1979), Barnes et al., Anal. Biochem. 102: 255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMY-CIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology 10: 163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody prepared from the cells can be purified using, for example, hydroxylapatite chromatography, gel electrophoresis, dialysis, DEAE-cellulose ion exchange chromatography, ammonium sulfate precipitation, salting out, and affinity chromatography, with affinity chromatography being the preferred purification technique.

Following any preliminary purification step (s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25 M salt).

Pharmaceutical Compositions

In some aspects, the disclosure is directed to a pharmaceutical composition comprising at least one PD-L1 binding molecule as disclosed herein and a pharmaceutically acceptable carrier.

Components of the Compositions

The pharmaceutical composition may optionally contain one or more additional pharmaceutically active ingredients, such as another antibody or a drug. The pharmaceutical compositions of the disclosure also can be administered in a combination therapy with, for example, another immune-stimulatory agent, anti-cancer agent, an antiviral agent, or a vaccine, such that the anti-PD-L1 antibody enhances the immune response against the vaccine. A pharmaceutically acceptable carrier can include, for example, a pharmaceutically acceptable liquid, gel or solid carriers, an aqueous medium, a non-aqueous medium, an anti-microbial agent, isotonic agents, buffers, antioxidants, anesthetics, suspending/dispersing agent, a chelating agent, a diluent, adjuvant, excipient or a nontoxic auxiliary substance, other known in the art various combinations of components or more.

Suitable components may include, for example, antioxidants, fillers, binders, disintegrating agents, buffers, preservatives, lubricants, flavorings, thickening agents, coloring agents, emulsifiers or stabilizers such as sugars and cyclodextrin. Suitable anti-oxidants may include, for example, methionine, ascorbic acid, EDTA, sodium thiosulfate, platinum, catalase, citric acid, cysteine, mercapto glycerol, thioglycolic acid, Mercapto sorbitol, butyl methyl anisole, butylated hydroxy toluene and/or propylgalacte. As disclosed in the present disclosure, the compositions of the present disclosure containing the antibody include one or more anti-oxidants such as methionine, to reduce the oxidization of the antibody. The oxidation reduction may prevent or reduce a decrease in binding affinity, thereby enhancing antibody stability and extended shelf life. Thus, in some embodiments, the present disclosure provides a composition comprising one or more antibodies and one or more anti-oxidants such as methionine. The present disclosure further provides a variety of methods, wherein an antibody is mixed with one or more anti-oxidants, such as methionine, so that the antibody thereof can be prevented from oxidation, to extend their shelf life and/or increased activity.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

Administration, Formulation and Dosage

The pharmaceutical composition of the disclosure may be administered in vivo, to a subject in need thereof, by various routes, including, but not limited to, oral, intravenous, intra-arterial, subcutaneous, parenteral, intranasal, intramuscular, intracranial, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms;

including, but not limited to, tablets, capsules, powders, granules, ointments, solutions, suppositories, enemas, injections, inhalants, and aerosols. The appropriate formulation and route of administration may be selected according to the intended application and therapeutic regimen.

Suitable formulations for enteral administration include hard or soft gelatin capsules, pills, tablets, including coated tablets, elixirs, suspensions, syrups or inhalations and controlled release forms thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilizers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Similarly, the particular dosage regimen, i.e., dose, timing and repetition, will depend on the particular individual and that individual's medical history, as well as empirical considerations such as pharmacokinetics (e.g., half-life, clearance rate, etc.).

Frequency of administration may be determined and adjusted over the course of therapy, and is based on reducing the number of proliferative or tumorigenic cells, maintaining the reduction of such neoplastic cells, reducing the proliferation of neoplastic cells, or delaying the development of metastasis. In some embodiments, the dosage administered may be adjusted or attenuated to manage potential side effects and/or toxicity. Alternatively, sustained continuous release formulations of a subject therapeutic composition may be appropriate.

It will be appreciated by one of skill in the art that appropriate dosages can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action that achieve the desired effect without causing substantial harmful or deleterious side-effects.

In general, the PD-L1 binding molecules may be administered in various ranges. In some embodiments, the PD-L1 binding molecules as provided herein may be administered at a therapeutically effective dosage of about 0.01 mg/kg to about 100 mg/kg (e.g., about 0.01 mg/kg, about 0.5 mg/kg, about 1 mg/kg, about 2 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg). In certain of these embodiments, the antibody is administered at a dosage of about 50 mg/kg or less, and in certain of these embodiments the dosage is 10 mg/kg or less, 5 mg/kg or less, 1 mg/kg or less, 0.5 mg/kg or less, or 0.1 mg/kg or less. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

In any event, the antibody of the disclosure is preferably administered as needed to subjects in need thereof. Determination of the frequency of administration may be made by persons skilled in the art, such as an attending physician based on considerations of the condition being treated, age of the subject being treated, severity of the condition being treated, general state of health of the subject being treated and the like.

In certain preferred embodiments, the course of treatment involving the antibody of the instant disclosure will comprise multiple doses of the selected drug product over a period of weeks or months. More specifically, the antibody of the instant disclosure may be administered once every day, every two days, every four days, every week, every ten days, every two weeks, every three weeks, every month, every six weeks, every two months, every ten weeks or every three months. In this regard, it will be appreciated that the dosages may be altered or the interval may be adjusted based on patient response and clinical practices.

Dosages and regimens may also be determined empirically for the disclosed therapeutic compositions in individuals who have been given one or more administration(s). For example, individuals may be given incremental dosages of a therapeutic composition produced as described herein. In selected embodiments, the dosage may be gradually increased or reduced or attenuated based respectively on empirically determined or observed side effects or toxicity. To assess efficacy of the selected composition, a marker of the specific disease, disorder or condition can be followed as described previously. For cancer, these include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer) or a tumorigenic antigen identified according to the methods described herein, a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of neoplastic condition, the stage of neoplastic condition, whether the neoplastic condition has begun to metastasize to other location in the individual, and the past and concurrent treatments being used.

Compatible formulations for parenteral administration (e.g., intravenous injection) may comprise the PD-L1 binding molecules as provided herein in concentrations of from about 10 µg/ml to about 100 mg/ml. In some embodiments, the concentrations of the PD-L1 binding molecule may comprise 20 µg/ml, 40 µg/ml, 60 µg/ml, 80 µg/ml, 100 µg/ml, 200 µg/ml, 300, µg/ml, 400 µg/ml, 500 µg/ml, 600 µg/ml, 700 µg/ml, 800 µg/ml, 900 µg/ml or 1 mg/ml. In other preferred embodiments, the concentration of the PD-L1 binding molecule comprise 2 mg/ml, 3 mg/ml, 4 mg/ml, 5 mg/ml, 6 mg/ml, 8 mg/ml, 10 mg/ml, 12 mg/ml, 14 mg/ml, 16 mg/ml, 18 mg/ml, 20 mg/ml, 25 mg/ml, 30 mg/ml, 35 mg/ml, 40 mg/ml, 45 mg/ml, 50 mg/ml, 60 mg/ml, 70 mg/ml, 80 mg/ml, 90 mg/ml or 100 mg/ml.

Applications of the Invention

The PD-L1 binding molecules of the present disclosure have numerous in vitro and in vivo utilities. For example, these molecules can be administered to cells in culture, in vitro or ex vivo, or to human subjects, e.g., in vivo, to enhance immunity in a variety of situations. The immune response can be augmented, stimulated or up-regulated.

Preferred subjects include human patients in need of enhancement of an immune response. The methods are particularly suitable for treating human patients having a disorder that can be treated by augmenting an immune response (e.g., the T-cell mediated immune response). In a particular embodiment, the methods are particularly suitable for treatment of cancer in vivo. To achieve antigen-specific enhancement of immunity, the anti-PD-L1 antibodies can be administered together with an antigen of interest or the antigen may already be present in the subject to be treated (e.g., a tumor-bearing or virus-bearing subject). When anti-PD-L1 antibodies are administered together with another agent, the two can be administered in either order or simultaneously.

The disclosure further provides methods for detecting the presence of PD-L1 antigen in a sample, or measuring the amount of human PD-L1 antigen, comprising contacting the sample, and a control sample, with the PD-L1 binding molecules, under conditions that allow for formation of a complex between the PD-L1 binding molecule and PD-L1. The formation of a complex is then detected, wherein a difference complex formation between the sample compared to the control sample is indicative of the presence of PD-L1 antigen in the sample. Moreover, the PD-L1 binding molecules of the disclosure can be used to purify human PD-L1 via immunoaffinity purification.

Treatment of Cancers

Conditions and disorders associated with PD-L1 can be an immunity-related disease or disorder.

In some embodiments, the PD-L1 associated conditions and disorders include tumors and cancers, comprising but not limited to breast, lung, colon, ovarian, melanoma, bladder, kidney, liver, salivary, stomach, gliomas, thyroid, thymic, epithelial, head and neck cancers, gastric and pancreatic cancer.

More specifically, the PD-L1 associated conditions and disorders include non-small cell lung cancer, small cell lung cancer, renal cell cancer, colorectal cancer, ovarian cancer, breast cancer, pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, leukemia, lymphomas, myelomas, mycoses fungoids, merkel cell cancer, and other hematologic malignancies, such as classical Hodgkin lymphoma (CHL), primary mediastinal large B-cell lymphoma, T-cell/histiocyte-rich B-cell lymphoma, EBV-positive and -negative PTLD, and EBV-associated diffuse large B-cell lymphoma (DLBCL), plasmablastic lymphoma, extranodal NK/T-cell lymphoma, nasopharyngeal carcinoma, and HHV8-associated primary effusion lymphoma, Hodgkin's lymphoma, neoplasm of the central nervous system (CNS), such as primary CNS lymphoma, spinal axis tumor, brain stem glioma. In certain embodiments, the tumors and cancers are metastatic, especially metastatic tumors expressing PD-L1.

The antibody may be used in combination with chemical therapies or radiotherapies.

Combined Use with Chemotherapies

The antibody may be used in combination with an anti-cancer agent, a cytotoxic agent or chemotherapeutic agent.

The term "anti-cancer agent" or "anti-proliferative agent" means any agent that can be used to treat a cell proliferative disorder such as cancer, and includes, but is not limited to, cytotoxic agents, cytostatic agents, anti-angiogenic agents, debulking agents, chemotherapeutic agents, radiotherapy and radiotherapeutic agents, targeted anti-cancer agents, BRMs, therapeutic antibodies, cancer vaccines, cytokines, hormone therapies, radiation therapy and anti-metastatic agents and immunotherapeutic agents. It will be appreciated that, in selected embodiments as discussed above, such anti-cancer agents may comprise conjugates and may be associated with the disclosed site-specific antibodies prior to administration. More specifically, In some embodiments selected anti-cancer agents will be linked to the unpaired cysteines of the engineered antibodies to provide engineered conjugates as set forth herein. Accordingly, such engineered conjugates are expressly contemplated as being within the scope of the instant disclosure. In other embodiments, the disclosed anti-cancer agents will be given in combination with site-specific conjugates comprising a different therapeutic agent as set forth above.

As used herein the term "cytotoxic agent" means a substance that is toxic to the cells and decreases or inhibits the function of cells and/or causes destruction of cells. In some embodiments, the substance is a naturally occurring molecule derived from a living organism. Examples of cytotoxic agents include, but are not limited to, small molecule toxins or enzymatically active toxins of bacteria (e.g., Diptheria toxin, *Pseudomonas* endotoxin and exo-toxin, Staphylococcal enterotoxin A), fungal (e.g., α-sarcin, restrictocin), plants (e.g., abrin, ricin, modeccin, viscumin, pokeweed anti-viral protein, saporin, gelonin, momoridin, trichosanthin, barley toxin, *Aleurites fordii* proteins, dianthin proteins, *Phytolacca mericana* proteins (PAPI, PAPII, and PAP-S), *Momordica charantia* inhibitor, curcin, crotin, *Saponaria officinalis* inhibitor, gelonin, mitegellin, restrictocin, phenomycin, neomycin, and the tricothecenes) or animals, (e.g., cytotoxic RNases, such as extracellular pancreatic RNases; DNase I, including fragments and/or variants thereof).

For the purposes of the instant disclosure a "chemotherapeutic agent" comprises a chemical compound that non-specifically decreases or inhibits the growth, proliferation, and/or survival of cancer cells (e.g., cytotoxic or cytostatic agents). Such chemical agents are often directed to intracellular processes necessary for cell growth or division, and are thus particularly effective against cancerous cells, which generally grow and divide rapidly. For example, vincristine depolymerizes microtubules, and thus inhibits cells from entering mitosis. In general, chemotherapeutic agents can include any chemical agent that inhibits, or is designed to inhibit, a cancerous cell or a cell likely to become cancerous or generate tumorigenic progeny (e.g., TIC). Such agents are often administered, and are often most effective, in combination, e.g., in regimens such as CHOP or FOLFIRI.

Examples of anti-cancer agents that may be used in combination with the site-specific constructs of the present disclosure (either as a component of a site specific conjugate or in an unconjugated state) include, but are not limited to, alkylating agents, alkyl sulfonates, aziridines, ethylenimines and methylamelamines, acetogenins, a camptothecin, bryostatin, callystatin, CC-1065, cryptophycins, dolastatin, duocarmycin, eleutherobin, pancratistatin, a sarcodictyin, spongistatin, nitrogen mustards, antibiotics, enediyne antibiotics, dynemicin, bisphosphonates, esperamicin, chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, erlotinib, vemurafenib, crizotinib, sorafenib, ibrutinib, enzalutamide, folic acid analogues, purine analogs, androgens, anti-adrenals, folic acid replenisher such as frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, an epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid, 2-ethylhydrazide, procarbazine, PSK® polysaccharide complex (JHS Natural Products, Eugene, OR), razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, chloranbucil; GEMZAR® gemcitabine; 6-thioguanine; mercaptopurine; methotrexate; platinum analogs, vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11), topoisomerase inhibitor RFS 2000; difluorometlhylornithine; retinoids; capecitabine; combretastatin; leucovorin; oxaliplatin; inhibitors of PKC-alpha, Raf, H-Ras, EGFR and VEGF-A that reduce cell proliferation and pharmaceutically acceptable salts, acids or derivatives of any of the above. Also included in this definition are anti-hormonal agents that act to regulate or inhibit hormone action on tumors such as anti-estrogens and selective estrogen receptor modulators, aromatase inhibitors that inhibit the enzyme aromatase, which regulates estrogen production in the adrenal glands, and anti-androgens; as well as troxacitabine (a 1,3-dioxolane nucleoside cytosine analog); antisense oligonucleotides, ribozymes such as a VEGF expression inhibitor and a HER2 expression inhibitor; vaccines, PROLEUKIN® rIL-2; LUIRTOTECAN® topoisomerase 1 inhibitor; ABARELIX® rmRH; Vinorelbine and Esperamicins and pharmaceutically acceptable salts, acids or derivatives of any of the above.

Combined Use with Radiotherapies

The present disclosure also provides for the combination of the antibody with radiotherapy (i.e., any mechanism for inducing DNA damage locally within tumor cells such as gamma-irradiation, X-rays, UV-irradiation, microwaves, electronic emissions and the like). Combination therapy using the directed delivery of radioisotopes to tumor cells is also contemplated, and the disclosed conjugates may be used in connection with a targeted anti-cancer agent or other targeting means. Typically, radiation therapy is administered in pulses over a period of time from about 1 to about 2 weeks. The radiation therapy may be administered to subjects having head and neck cancer for about 6 to 7 weeks.

Optionally, the radiation therapy may be administered as a single dose or as multiple, sequential doses.

Diagnosis

The disclosure provides in vitro and in vivo methods for detecting, diagnosing or monitoring proliferative disorders and methods of screening cells from a patient to identify tumor cells including tumorigenic cells. Such methods include identifying an individual having cancer for treatment or monitoring progression of a cancer, comprising contacting the patient or a sample obtained from a patient (either in vivo or in vitro) with an antibody as described herein and detecting presence or absence, or level of association, of the antibody to bound or free target molecules in the sample. In some embodiments, the antibody will comprise a detectable label or reporter molecule as described herein.

In some embodiments, the association of the antibody with particular cells in the sample can denote that the sample may contain tumorigenic cells, thereby indicating that the individual having cancer may be effectively treated with an antibody as described herein.

Samples can be analyzed by numerous assays, for example, radioimmunoassays, enzyme immunoassays (e.g. ELISA), competitive-binding assays, fluorescent immunoassays, immunoblot assays, Western Blot analysis and flow cytometry assays. Compatible in vivo theragnostic or diagnostic assays can comprise art recognized imaging or monitoring techniques, for example, magnetic resonance imaging, computerized tomography (e.g. CAT scan), positron tomography (e.g., PET scan), radiography, ultrasound, etc., as would be known by those skilled in the art.

Pharmaceutical Packs and Kits

Pharmaceutical packs and kits comprising one or more containers, comprising one or more doses of the antibody are also provided. In some embodiments, a unit dosage is provided wherein the unit dosage contains a predetermined amount of a composition comprising, for example, the antibody, with or without one or more additional agents. For other embodiments, such a unit dosage is supplied in single-use prefilled syringe for injection. In still other embodiments, the composition contained in the unit dosage may comprise saline, sucrose, or the like; a buffer, such as phosphate, or the like; and/or be formulated within a stable and effective pH range. Alternatively, in some embodiments, the conjugate composition may be provided as a lyophilized powder that may be reconstituted upon addition of an appropriate liquid, for example, sterile water or saline solution. In certain preferred embodiments, the composition comprises one or more substances that inhibit protein aggregation, including, but not limited to, sucrose and arginine. Any label on, or associated with, the container(s) indicates that the enclosed conjugate composition is used for treating the neoplastic disease condition of choice.

The present disclosure also provides kits for producing single-dose or multi-dose administration units of site-specific conjugates and, optionally, one or more anti-cancer agents. The kit comprises a container and a label or package insert on or associated with the container. Suitable containers include, for example, bottles, vials, syringes, etc. The containers may be formed from a variety of materials such as glass or plastic and contain a pharmaceutically effective amount of the disclosed conjugates in a conjugated or unconjugated form. In other preferred embodiments, the container(s) comprise a sterile access port (for example the container may be an intravenous solution bag or a vial having a stopper pierceable by a hypodermic injection needle). Such kits will generally contain in a suitable container a pharmaceutically acceptable formulation of the engineered conjugate and, optionally, one or more anti-cancer agents in the same or different containers. The kits may also contain other pharmaceutically acceptable formulations, either for diagnosis or combined therapy. For example, in addition to the antibody, such kits may contain any one or more of a range of anti-cancer agents such as chemotherapeutic or radiotherapeutic drugs; anti-angiogenic agents; anti-metastatic agents; targeted anti-cancer agents; cytotoxic agents; and/or other anti-cancer agents.

More specifically the kits may have a single container that contains the disclosed the antibody, with or without additional components, or they may have distinct containers for each desired agent. Where combined therapeutics are provided for conjugation, a single solution may be pre-mixed, either in a molar equivalent combination, or with one component in excess of the other. Alternatively, the conjugates and any optional anti-cancer agent of the kit may be maintained separately within distinct containers prior to administration to a patient. The kits may also comprise a second/third container means for containing a sterile, pharmaceutically acceptable buffer or other diluent such as bacteriostatic water for injection (BWFI), phosphate-buffered saline (PBS), Ringer's solution and dextrose solution.

When the components of the kit are provided in one or more liquid solutions, the liquid solution is preferably an aqueous solution, with a sterile aqueous or saline solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

As indicated briefly above the kits may also contain a means by which to administer the antibody and any optional components to a patient, e.g., one or more needles, I.V. bags or syringes, or even an eye dropper, pipette, or other such like apparatus, from which the formulation may be injected or introduced into the animal or applied to a diseased area of the body. The kits of the present disclosure will also typically include a means for containing the vials, or such like, and other component in close confinement for commercial sale, such as, e.g., injection or blow-molded plastic containers into which the desired vials and other apparatus are placed and retained.

Sequence Listing Summary

Appended to the instant application is a sequence listing comprising a number of nucleic acid and amino acid sequences. The following Table A provides a summary of the included sequences.

TABLE A

| SEQ ID NO. | Description |
|---|---|
| 1 | CDR1 of AP3R2-1A3-z12 |
| 2 | CDR2 of AP3R2-1A3-z12 |
| 3 | CDR3 of AP3R2-1A3-z12 |
| 4 | Full-length sequence of the VHH of AP3R2-1A3-z12 |
| 5 | Nucleotide sequence encoding the VHH of AP3R2-1A3-z12 |

EXAMPLES

The present disclosure, thus generally described, will be understood more readily by reference to the following Examples, which are provided by way of illustration and are not intended to be limiting of the instant disclosure. The Examples are not intended to represent that the experiments below are all or the only experiments performed.

Example 1

Preparation of Materials

1. Preparation of Materials
1.1 Commercial Materials
Information on the commercially available materials used in the examples is provided in Table 1. The materials for which the source is not specified are also commercially available or can be easily prepared by those skilled in the art according to standard molecular or genetic biological methods.

TABLE 1

| Commercial materials | | |
|---|---|---|
| Materials | Vendor | Cat. |
| PE mouse anti-human CD274 Ab | eBioscience | Cat. #12-5983-42 |
| PE rat anti-mouse CD274 Ab | eBioscience | Cat. #12-4317-87 |
| PE goat anti-mouse IgG Fc | Abcam | Cat. #ab98742 |
| R-PE goat anti-human IgG Fc | Jackson Immuno Research | Cat. #109-115-098 |
| PE goat anti-mouse IgG Fc | Abcam | Cat. #Ab98742 |
| Human PD-L1, ECD, mFc tag | Sino Biological | Cat. #10084-H05H |
| SA-PE | eBioscience | Cat. #12-4317-87 |
| HRP goat anti-human IgG Fc | Bethyl | Cat. #A80-304P |
| Ficoll-Paque ™ PLUS | GE Healthcare | Cat. #17-1440-02 |
| CD14 MicroBeads, human | Milteny | Cat. #130-050-201 |
| Human CD4+ T Cell Enrichment kit | STEMCELL | Cat. #19052 |
| Recombinant human GM-CSF | Amoytop Biotech | Cat. #S10980039 |
| Recombinant human IL-4 | R&D | Cat. #204-IL-010 |
| Standard recombinant human IFN-γ | PeproTech | Cat. #300-02 |
| Human IFN-γ capture antibody | Pierce | Cat. #M700A |
| Human IFN-γ detection antibody | Pierce | Cat. #M701B |
| SA-HRP | Invitrogen | Cat. #SNN1004 |
| Standard recombinant human IL-2 | R&D | Cat. #202-IL-010 |
| Human IL-2 capture antibody | R&D | Cat. #MAB602 |
| Human IL-2 detection antibody | R&D | Cat. #BAF202 |
| Mouse IL-2 ELISA kit | BD | Cat. #2614KI |
| CMV pp65 peptide | Miltenyi Biotec | Cat. #130-093-435 |
| LPS | Sigma | Cat. #L5418 |

TABLE 1-continued

| Commercial materials | | |
|---|---|---|
| Materials | Vendor | Cat. |
| H3-thymidine | PerkinElmer | Cat. #NET027001MC |
| MicroScint-20 | PerkinElmer | Cat. #6013621 |
| Herceptin | Roche | Lot. #N3550 |
| Human Serum Complement | Quidel | Cat. #A112 |
| Cytotoxicity Detection Kit | Roche | Cat. #11644793001 |
| CellTiter Glo Kit | Promega | Cat. #G7571 |
| BT-474 cell line | ATCC | Cat. # HTB-20 |
| Raji cell line | ATCC | Cat. #CCL-86 |
| Lipofectamine ™ 2000 Transfection Reagent | Invitrogen | Cat. #11668019 |
| Ham's F-12K (Kaighn's) Medium | Gibco | Cat. #21127022 |
| FreeStyle ™ 293 Expression Medium | Gibco | Cat. #12338002 |
| Fetal Bovine Serum | HyClone | Cat. #SV30087.03 |
| Blasticidin | Gibco | Cat. #R21001 |

1.2 Material Code

The codes or abbreviation for the materials including benchmark antibodies, the extracellular domains and the cells are summarized in Table 2.

TABLE 2

| Material Code | |
|---|---|
| Materials Name | Code |
| Benchmark antibody 6, same sequence with Imfinzi | BMK6.uIgG1K(LFLEPS) or W315-BMK6.uIgG1K(LFLEPS) |
| Benchmark antibody 6, variable region of Imfinzi conjugated with human IgG4 constant region | BMK6.hIgG4 or W315-BMK6.hIgG4 |
| Benchmark antibody 8, same sequence with Tecentriq | BMK8.uIgG1K(RKNA) or W315-BMK8.uIgG1K(RKNA) |
| Benchmark antibody 8, variable region of Tecentriq conjugated with human IgG4 constant region | BMK8.hIgG4 or W315-BMK8.hIgG4 |
| Benchmark antibody 9, same sequence with KN035 | BMK9.Fc(IgG1) or W315-BMK9.Fc(IgG1) |
| Benchmark antibody 9, variable region of KN035 conjugated with human IgG4 constant region | BMK9.Fc(IgG4) or W315-BMK9.Fc(IgG4) |
| Human IgG1 isotype control | hIgG1 Isotype |
| Human IgG4 isotype control | hIgG4 Isotype |
| Human PD-1 extracellular domain, mFc tag | W305-hPro1.ECD.mFc |
| Mouse PD-1 extracellular domain, mFc tag | W305-mPro1.ECD.mFc |
| Human PD-L1 extracellular domain, mFc tag | W315-hPro1.ECD.mFc |
| Mouse PD-L1 extracellular domain, mFc tag | W315-mPro1.ECD.mFc |
| Human PD-L1-expressing CHO-K1 cell | W315-CHO-K1.hPro1.C11 |
| Mouse PD-L1-expressing 293F cell | W315-293F.mPro1.C1 |
| Human CD80-expressing CHO-K1 cell | CHO-K1.CD80.B9 |
| Cynomolgus monkey PD-L1-expressing 293F cell | W315-293F.cynoPro1.2A2 |

2. Production of Antigens

Antigens W305-hPro1.ECD.mFc (NP_005009.2), W315-hPro1.ECD.mFc (NP_054862.1) and W305-mPro1.ECD.mFc (NP_032824.1), W315-mPro1.ECD.mFc (NP_068693.1) were prepared according to standard molecular biological methods. Briefly, DNA sequences encoding the extracellular domain segment of the antigens were synthesized in GENEWIZ (Suzhou, China) based on the corresponding accession number of each antigen gene and then sub-cloned into pcDNA3.3 expression vectors (Thermo Fisher Scientific) with mouse Fc tag at the C-terminus. The recombinant plasmids were then transfected into Expi293 cells (Invitrogen-A14527). The cell culture was grown in a humidified platform shaker with the rotation rate at 150 rpm. The temperature was maintained at 37° C. with $CO_2$ level at 8%. After five days of incubation, the supernatant was collected and filtered for purification.

3. Production of Benchmark Antibodies

The variable sequence of anti-human PD-L1 control antibodies BMK6.uIgG1K (LFLEPS) and BMK6.hIgG4 was synthesized based on the sequence of clone MEDI4736 from PCT application WO2015036499 filed by MedImmune; BMK6. uIgG1K (LFLEPS) and BMK6.hIgG4 were prepared based on the sequence of commercially available Imfinzi. The variable sequence of BMK8. uIgG1K (RKNA) and BMK8.hIgG4 was prepared based on the sequence of clone YW243.55.570 from PCT application WO2010077634 filed by Roche. BMK8. uIgG1K (RKNA) and BMK8.hIgG4 were prepared based on the sequences of Tecentriq (commercially available from Genentech). BMK9.Fc(IgG1) was prepared based on the sequence of clone KN035 from PCT application WO2017020802 filed by Suzhou ALPHAMAB. The human IgG1 and IgG4 isotype control antibodies were discovered by WuXi Biologics Discovery HD group and prepared by PS group, which share the same variable region.

The genes were synthesized in GENEWIZ (Suzhou, China), and then subcloned into modified pcDNA3.3 expression vectors (Thermal Fisher Scientifics). Expi293 cells (Invitrogen-A14527) were transfected with the purified expression vector. Cells were cultured for 5 days and supernatant was collected for protein purification using Protein A column (GE Healthcare, 175438). The purified proteins were analyzed by SDS-PAGE and SEC, and then stored at −80° C.

4. Establishment of Stable Cell Lines/Cell Pool

Human PD-L1-expressing cell line (W315-CHO-K1. hPro1. C11), mouse PD-L1-expressing cell line (W315-293F.mPro1.C1), cynomolgus monkey PD-L1-expressing cell line (W315-293F.cynoPro1.2A2), human CD80-expressing cell line (CHO-K1.CD80.B9) were generated by WuXi Biologics Discovery PS group.

For human PD-L1 (NP_054862.1) and CD80 (NP_005182.1) high expression cell line construction, the genes of human PD-L1 and CD80 were respectively inserted into expression vector pcDNA 3.3. Each expression vector was then transfected into CHO-K1 cells respectively. Briefly, one day prior to transfection, $5 \times 10^5$ CHO-K1 cells were plated into one well of 6-well tissue culture plate and incubated at 5% $CO_2$ and 37° C. The cells were fed with 3 ml of fresh media F12-K with 10% FBS. Transfection reagents were prepared in a 1.5 mL tube, including 4 μg of DNA mixed with 10 μg of Lipofectamine 2000 and Opti-MEM medium to a final volume of 200 μl. The solution in the tube pipette was added to the cells drop by drop. Six to eight hours after transfection, cells were washed with PBS and feed with 3 ml of fresh media. Expressing cells were harvested with trypsin 24-48 hours after transfection and plated to T75 flask in selective media (F12-K with 10% FBS and 10 μg/ml Blasticidin). Stable single cell clones were isolated by limiting dilution.

For mouse and cynomolgus monkey PD-L1 high expression cell line construction, the genes of mouse PD-L1 (NP_068693.1) and cynomolgus monkey PD-L1 (XP_015292694.1) were respectively inserted into expression vector pcDNA 3.3. Each expression vector was then transfected into 293F cells respectively. Briefly, cells were counted and diluted to a density of $1.2 \times 10^6$/ml into a 125 ml flask and shaken at 5% $CO_2$ and 37° C. The cells were fed with 30 ml of fresh media Freestyle293. Transfection reagents were prepared in a 15 ml tube, including 30 μg of DNA mixed with 75 μl of Lipofectamine 2000 and Opti-MEM medium to a final volume of 3 ml. The solution in the tube pipette was added to the cells drop by drop. Expressing cells were harvested after transfection and transferred to 125 ml flask in selective media (Freestyle293 and 4 μg/ml Blasticidin). Stable single cell clones were isolated by limiting dilution.

Example 2

Production of VHH and VHH-Fc Fusion Antibodies
1. Immunization

To induce a humoral immune response directed towards PD-L1 in camelid animals, the animals were subcutaneously injected alternately with human and mouse PD-L1 ECD proteins (see "2. Production of Antigens" in Example 1) for 8 doses at 1 to 3 weeks intervals. The dose ranged from 50 ug to 200 ug per injection.

2. Serum Titer Detection

After immunization, the anti-PD-L1 specific antibody serum titer presented in animal sera was determined by ELISA. Briefly, ELISA plates (Nunc, Rochester, MN, USA) were coated with 1 μg/ml of recombinant his tagged human and mouse PD-L1 ECD protein, respectively, and incubated overnight at 4° C. After blocking and washing, serial dilutions of pre-immune or immune sera were added and incubated at room temperature for 2 h, then followed with goat anti-Llama IgG-HRP (Novas Biologicals, Littleton, CO, USA) at room temperature for 1 h. After washing, TMB substrate (Invitrogen, Carlsbad, CA, USA) was added and the reaction was stopped by 2 M HCl. The absorbance at 450 nm was read using a microplate reader (Molecular Device, Sunnyvale, CA, USA).

3. Phage Library Construction 50 ml blood samples were collected at 6-7 days after the last two injections, respectively. Peripheral blood mononuclear cells (PBMCs) were purified by density gradient centrifugation on Ficoll-Paque PLUS (GE Healthcare, Little Chalfont, UK), resulting in the isolation of approximately $1 \times 10^8$ PBMCs. Total RNA was extracted from these PBMCs and transcribed into cDNA using an oligo-dT primer and SuperScript III First-Strand Synthesis SuperMix System (Invitrogen, Carlsbad, CA, USA) according to the manufacturers' recommendations.

The purified cDNA was then used as a template to amplify the repertoire of Ig heavy chain-encoding gene segments with the use of signal peptide domain specific primers and CH2 domain specific primers. This amplification resulted in PCR fragments of approximately 900 bp (representing conventional IgGs) and 700 bp (representing heavy-chain IgGs that lack a CH1 domain). The two classes of heavy chain encoding genes were then size-separated on agarose gels and the genes encoding heavy-chain only IgG were purified by QIAquick Gel Extraction Kit (Qiagen, Hilden, Germany). The purified fragments were used as templates to amplify the VHH repertoire with the use of framework1 (FR1) and framework4 (FR4) specific primer pairs. This amplification procedure introduced a Sfi I restriction site at the 5' end of FR1 and a Not I restriction site at the 3' end of FR4. The repertoire of PCR-amplified VI-11-1 genes of about 300-400 bp were loaded on agarose gels and purified by QIAquick Gel Extraction Kit. The purified fragments were then cut with Sfi I and Not I and purified by QIAquick PCR Purification Kit (Qiagen, Hilden, Germany). The VHH gene fragments were finally ligated in phagemid vector pFL249 (Nanjing GenScript) and electrotransformed into E. coli TG1. After transformation, the TG1 cells were cultured in SOC medium with shaking at 200 rpm for 1 h, then the E. coli TG1 were plated onto plates containing solid 2YT medium supplemented with 100 μg/mL Carb and 1% (w/v) glucose, and cultured at 37° C. overnight. The next day, the colonies were scraped into liquid 2YT medium supplemented with ⅓ (v/v) of 80% glycerol and were stored at −80° C.

4. Phage Display Selection of Anti-PD-L1 Specific VHH Fragments

To select VHH fragments that would effectively bind to PD-L1, the method of protein panning was employed.

Briefly, 20 μg of recombinant his-tagged human PD-L1 ECD protein was immobilized in 5 ml immune tube (Nunc, Rochester, MN, USA) overnight at 4° C. with shaking at 400 rpm. The next day, after washing away unbound protein, the tube was blocked with 10% skim milk for 1 h at 25° C. Approximately $10^{12}$ cfu phages from the immune phage libraries was added into non-coated immune tube blocked with 10% skim milk to deplete the non-specifically bound phage, then phages treated as described above were added into the tube and incubated at 25° C. for 2 h. After extensive washing with PBST (phosphate buffered solution), the non-specifically adsorbed phages were discarded and the target specifically bound phages were eluted by Glycine-HCl (pH2.2) and then neutralized by 1 M Tris-HCl (pH8.0) for infection of exponentially growing TG1 cells. The infected TG1 cells were plated on 2YT agar plates containing 2% (w/v) glucose and 100 µg/ml ampicillin and cultured overnight at 37° C. On the next day, the colonies were scraped off the plate with 3 ml 2YT and frozen at –80° C. by adding in ⅓ (v/v) 80% glycerol. The scraped bacteria libraries were inoculated into 2YT-Carb contain 100 µg/ml ampicillin, infected with helper phage M13K07 in 2YT medium with 50 µg/ml kanamycin and 1 mM IPTG for phage rescue and used as input for the next round of panning.

5. VHH Protein Expression and Screening

After desired panning steps, phage infected TG1 cell colonies grown on the plates were scraped and pFL249 phagemid containing VHH fragments were extracted. The VHH fragments were cloned by digestion of pFL249 plasmids with Sfi I and Not I and then ligated into expression vector pETbac containing genes of hexa-histidine- and c-Myc-tag. The ligation products were transformed into *E. coli* BL21 (DE3) competent cells and then cultured in ZYM-5052 medium at 25° C. for 48 h with shaking at 230 rpm. Then the bacterial culture supernatants were collected for ELISA or FACS tests.

ELISA was used as the first screening method to test the binding of VHH to human PD-L1 ECD protein. Briefly, 96-well plates (Nunc, Rochester, MN, USA) were coated with recombinant his-tagged human PD-L1 ECD protein overnight at 4° C. After blocking and washing, the BL21 *E. coli* supernatants were transferred to the coated plates and incubated at room temperature for 1 h. The plates were then washed and subsequently incubated with the secondary antibody Goat Anti-c-Myc-HRP (Bethyl, Montgomery, TX, USA) for 1 h. After washing, TMB substrate was added and the reaction was stopped by 2 M HCl. The absorbance at 450 nm was read by using a microplate reader (Molecular Device, Sunnyvale, CA, USA).

In order to confirm the native binding to human PD-L1 and blocking its interaction with PD1 on conformational PD-L1 molecules expressed on cell membrane, flow cytometry analysis was performed with CHOK1.PD-L1 cells. The cells were firstly incubated with the *E. coli* culture supernatant samples and ligand in 96-well U-bottom plates (BD, Franklin Lakes, NJ, USA) at a density of $1\times10^6$ cells/well at 4° C. for 1 h, then with a secondary antibody Goat Anti-c-Myc-PE (Bethyl, Montgomery, TX, USA) at 4° C. for 30 min. 2 times of washings were applied between each steps and the cells were resuspended in 1×PBS/1% BSA for flow cytometry analysis (IntelliCyt, Albuquerque, NM, USA).

6. Chimeric VHH-Fc (hIgG1) Protein Production

The clones of interest were converted to VHH-Fc (hIgG1) fusion antibodies. Briefly, the VHH genes were PCR amplified from the pET-bac vectors using VHH-specific cloning primers containing appropriate restriction sites then cloned by fusion into a modified expression pcDNA3.3 vector containing Fc of human hIgG1 to create corresponding clones of VHH-Fc (hIgG1) chimeric antibody. 293F or Expi293 cells were transiently transfected with the vector for antibody expression. The cell culture supernatants containing antibodies were harvested and purified using Protein A chromatography.

Example 3

Antibody Humanization

After ELISA and FACS screening, one VHH lead with desired affinity and specificity to PD-L1 was selected for humanization. "Best Fit" approach was used to humanize VHH chains.

Amino acid sequences of VHH framework regions were blasted against human germline V-gene database, and humanized VHH sequences were generated by replacing human CDR sequences in the top hit with VHH CDR sequences using Kabat CDR definition. Certain residues in the framework region were back-mutated to that of VHH in order to maintain the affinity. Humanized genes were back-translated, codon optimized for mammalian expression, and synthesized by GENEWIZ. After testing on PD-L1 binding using SPR, the VHH variant AP3R2-1A3-z12 was selected as humanized antibody lead. The sequence information thereof is provided in Table A and the sequence listing (see SEQ ID Nos: 4 (amino acid sequence) and 5 (nucleotide sequence)).

The gene of VHH AP3R2-1A3-z12 was cloned into a modified pcDNA3.3 vector containing Fc of human hIgG1 or human IgG4 to create corresponding clones of VHH-Fc (hIgG1) or VHH-Fc(hIgG4) for further characterization. The humanized clones were named as AP3R2-1A3-z12-hIgG1 or AP3R2-1A3-z12-hIgG4. In the disclosure and figures, the humanized antibody AP3R2-1A3-z12-hIgG1 is also presented by W3156-AP3R2-1A3-z12-hIgG1 and the humanized antibody AP3R2-1A3-z12-hIgG4 is also presented by W3156-AP3R2-1A3-z12-hIgG4. The two humanized antibodies are collectively called as "W3156 antibodies" in the disclosure.

Example 4

In Vitro Characterization

1. Binding of AP3R2-1A3-z12-hIgG1 to Human, Mouse, and Cynomolgus Monkey PD-L1 as Measured by FACS 1.1 Human PD-L1 Binding Human PD-L1 transfected W315-CHO-K1.hPro1.C11 cells were plated at $1\times10^5$ cells/well into 96-well U-bottom plate (BD) and incubated with various concentrations of anti-PD-L1 antibodies (4-fold serially diluted from 133.3 nM to 0.008 nM) at 4° C. for 1 hour. After washing with 1×PBS/1% BSA, the secondary antibody PE-labeled goat anti-human IgG was applied and incubated with cells at 4° C. for 1 hour. Anti-human PD-L1 antibodies BMK6.hIgG4, BMK8.hIgG4 and BMK9.Fc (IgG1) were used as positive control. Human IgG1 and IgG4 isotype antibodies were used as negative control. The cells were then washed and resuspended in 1×PBS/1% BSA. MFI of the cells was measured by a flow cytometer (BD) and analyzed by FlowJo (version 7.6.1). Data were shown in FIG. 1A and Table 3.

TABLE 3

| EC50 values of the binding between antibodies and human PD-L1 | |
|---|---|
| Abs | EC50 (nM) |
| AP3R2-1A3-z12-hIgG1 | 0.458 |
| BMK6.hIgG4 | 0.304 |

TABLE 3-continued

| EC50 values of the binding between antibodies and human PD-L1 | |
| --- | --- |
| Abs | EC50 (nM) |
| BMK8.hIgG4 | 0.562 |
| BMK9.Fc (IgG1) | 0.456 |

As shown in FIG. 1A and Table 3, AP3R2-1A3-z12-hIgG1 binds to cell surface human PD-L1 with an EC50 comparable to that of BMK antibodies.

1.2 Mouse PD-L1 Binding

Mouse PD-L1 transfected W315-293F.mPro1.C1 cells were plated at $2\times10^5$ cells/well into 96-well U-bottom plate and incubated with various concentrations of anti-PD-L1 antibodies (3-fold serially diluted from 133.3 nM to 0.0068 nM) at 4° C. for 1 hour. After washing with 1×PBS/1% BSA, the secondary antibody PE-labeled goat anti-human IgG was applied and incubated with cells at 4° C. for 1 hour. Anti-human PD-L1 antibodies BMK8.hIgG4 and BMK9.Fc (IgG1) were used as control antibodies. Human IgG1 and IgG4 isotype antibodies were used as negative control. The cells were then washed and resuspended in 1×PBS/1% BSA. MFI of the cells was measured by a flow cytometer (BD) and analyzed by FlowJo (version 7.6.1). Data were shown in FIG. 1B and Table 4.

TABLE 4

| EC50 values of the binding between antibodies and mouse PD-L1 | |
| --- | --- |
| Abs | EC50 (nM) |
| AP3R2-1A3-z12-hIgG1 | 1.241 |
| BMK9.Fc (IgG1) | — |
| BMK8.hIgG4 | 1.477 |

As shown in FIG. 1B and Table 4, AP3R2-1A3-z12-hIgG1 binds to cell surface mouse PD-L1 with an EC50 comparable to that of BMK8 Ab.

1.3 Cynomolgus Monkey PD-L1 Binding

Cynomolgus monkey PD-L1 transfected 293F.cynoPro1 cells were plated at $2\times10^5$ cells/well into 96-well U-bottom plate and incubated with various concentrations of anti-PD-L1 antibodies (3-fold serially diluted from 133.3 nM to 0.0068 nM) at 4° C. for 1 hour. After washing with 1×PBS/

1% BSA, the secondary antibody PE-labeled goat anti-human IgG was applied and incubated with cells at 4° C. for 1 hour. Anti-human PD-L1 antibodies BMK6.hIgG4, BMK8.hIgG4 and BMK9.Fc (IgG1) were used as control antibodies. Human IgG1 and IgG4 isotype antibodies were used as negative control. The cells were then washed and resuspended in 1×PBS/1% BSA. MFI of the cells was measured by a flow cytometer (BD) and analyzed by FlowJo (version 7.6.1). Data were shown in FIG. 1C and Table 5.

TABLE 5

| EC50 values of the binding between antibodies and cynomolgus monkey PD-L1 | |
| --- | --- |
| Abs | EC50 (nM) |
| AP3R2-1A3-z12-hIgG1 | 2.056 |
| BMK9.Fc (IgG1) | 2.326 |
| BMK6.hIgG4 | 2.649 |
| BMK8.hIgG4 | 2.189 |

As shown in FIG. 1C and Table 5, AP3R2-1A3-z12-hIgG1 binds to cell surface monkey PDL-1 with an EC50 comparable to that of BMK Abs.

2. Full Kinetic Affinity (SPR)

Antibodies binding affinities to his-tagged human PD-L1 (R&D-9049-B7), his-tagged cynomolgus PD-L1 (Sino Biological-90251-C08H) and his-tagged mouse PD-L1 (Sino Biological-50010-M08H) were detected by surface plasmon resonance (SPR) assay using the software ProteOn. Testing antibody was captured on anti-human IgG Fc antibody immobilized GLM chip (Bio-rad). The chip was rotated 90° and washed with running buffer until the baseline is stable. hPro1.ECD.His, cynoPro1.ECD.His and mPro1-ECD-His at different concentrations was injected over the sensor chip at a flow rate of 100 uL/min for an association phase of 120 s, followed by 240-800 s dissociation. The chip was regenerated by 10 mM glycine (pH 1.5) following every dissociation phase.

The sensorgrams for reference channel L1 and buffer channel A6 were subtracted from the test sensorgrams. The experimental data were fitted by 1:1 binding model. Molecular weight of 40 kDa was used to calculate the molar concentration of analyte hPro1.ECD.His (R&D), cynoPro1.ECD.His and mPro1-ECD-His.

Data were shown in Table 6.

TABLE 6

| | Affinity | | | |
| --- | --- | --- | --- | --- |
| Ligand | Analyte | ka (1/Ms) | kd (1/s) | $K_D$ (M) |
| AP3R2-1A3-z12-hIgG4 | hPro1.ECD.His (human PD-L1 ECD) | $1.85 \times 10^6$ | $3.85 \times 10^{-4}$ | $2.08 \times 10^{-10}$ |
| | cynoPro1.ECD.His (cyno PD-L1 ECD) | $1.91 \times 10^6$ | $4.78 \times 10^{-4}$ | $2.51 \times 10^{-10}$ |
| | mPro1-ECD-His (mouse PD-L1 ECD) | $5.89 \times 10^5$ | $1.14 \times 10^{-2}$ | $1.94 \times 10^{-8}$ |

3. Binding Affinity to Cell Surface PD-L1 (FACS)

Binding affinities of testing antibodies to cell surface human, cynomolgus and mouse PD-L1 were determined by flow cytometry on the engineering cell lines, respectively. The cells were transferred in to 96-well U-bottom plates (BD) at a density of $5 \times 10^4$ cells/well. Antibodies to be tested were 1: 2-fold serially diluted in 1% BSA/1×PBS and incubated with cells at 4° C. for 1 hr. Then, the plates were centrifuged at 1500 rpm for 4 mins and the supernatant was discarded. The secondary antibody, Alexa647 conjugated goat anti-human IgG Fc (Jackson, Cat No. 109-605-098, Lot No. 121363), was added to re-suspend cells and incubated at 4° C. in the dark for 30 min. The cells were washed once and re-suspended in 100 µL 1% BSA/1×PBS, then measured by flow cytometry (BD Canto II) and analyzed by FlowJo. Fluorescence intensity was converted to bound molecules/cell based on the quantitative beads (Quantum™ MESF Kits, Bangs Laboratories). $K_D$ value was calculated by Graphpad Prism5.

Data were shown in Table 7-1, Table 7-2 and Table 7-3.

TABLE 7-1

| Human PD-L1 | AP3R2-1A3-z12-hIgG1 | BMK6.hIgG4 | BMK8.hIgG4 | BMK9.Fc(IgG4) |
|---|---|---|---|---|
| Bmax | $3.0 \times 10^{-10}$ | $2.7 \times 10^{-10}$ | $3.3 \times 10^{-10}$ | $2.8 \times 10^{-10}$ |
| $K_D$ | $2.6 \times 10^{-10}$ | $1.5 \times 10^{-10}$ | $5.3 \times 10^{-10}$ | $2.4 \times 10^{-10}$ |
| $r^2$ | 0.98 | 0.93 | 1.00 | 1.00 |

Affinity to cell surface human PD-L1

TABLE 7-2

Affinity to cell surface cynomolgus PD-L1 (cynoPD-L1)

| cynoPD-L1 | AP3R2-1A3-z12-hIgG1 | BMK6.hIgG4 | BMK8.hIgG4 |
|---|---|---|---|
| Bmax | $7.1 \times 10^{-9}$ | $1.6 \times 10^{-8}$ | $8.8 \times 10^{-9}$ |
| $K_D$ | $7.3 \times 10^{-9}$ | $2.1 \times 10^{-8}$ | $1.6 \times 10^{-8}$ |
| $r^2$ | 0.99 | 0.99 | 0.97 |

TABLE 7-3

Affinity to cell surface mouse PD-L1

| Mouse PD-L1 | AP3R2-1A3-z12-hIgG1 | BMK8.hIgG4 |
|---|---|---|
| Bmax | $7.2 \times 10^{-10}$ | $8.3 \times 10^{-10}$ |
| $K_D$ | $6.9 \times 10^{-10}$ | $1.7 \times 10^{-9}$ |
| $r^2$ | 0.96 | 0.96 |

As shown in Table 7-1, Table 7-2 and Table 7-3, the binding affinities of AP3R2-1A3-z12-hIgG1 to cell surface human, cynomolgus and mouse PD-L1 are better/comparable to that of BMK Abs.

4. Blocking of the Binding to PD-L1 or CD80

4.1 Human PD-1/PD-L1 Blocking as Measured by FACS

Human PD-L1 transfected W315-CHO-K1.hPro1.C11 cells were transferred into 96-well U-bottom plates at a density of $1 \times 10^5$ cells/well. Various concentrations of antibodies (4-fold serially diluted from 266.7 nM to 0.016 nM) and constant concentration of human PD-1 ECD protein (hPro1.ECD.mFc) of 5 µg/mL were pre-mixed and incubated with the cells at 4° C. for 1 hour. After washing with 1×PBS/1% BSA, the secondary antibody PE-labeled goat anti-mouse IgG was applied and incubated with cells at 4° C. for 1 hour. Anti-human PD-L1 antibodies BMK6.hIgG4, BMK8.hIgG4 and BMK9.Fc (IgG1) were used as positive control. Human IgG1 and IgG4 isotype antibodies were used as negative control. The cells were then washed and resuspended in 1×PBS/1% BSA. MFI of the cells was measured by a flow cytometer (BD) and analyzed by FlowJo (version 7.6.1). Data were shown in FIG. 2A and Table 8.

TABLE 8

IC50 of the inhibition of binding between human PD-1 to PD-L1

| Abs | IC50 (nM) |
|---|---|
| AP3R2-1A3-z12-hIgG1 | 0.871 |
| BMK6.hIgG4 | 0.469 |
| BMK8.hIgG4 | 0.598 |
| BMK9.Fc (IgG1) | 0.798 |

4.2 Mouse PD-1/PD-L1 Blocking as Measured by FACS

Mouse PD-L1 transfected W315-293F.mPro1.C1 cells were transferred into 96-well U-bottom plates at a density of $2 \times 10^5$ cells/well. Various concentrations of anti-PD-L1 antibodies (3-fold serially diluted from 133.3 nM to 0.068 nM) and constant concentration of mouse PD-1 ECD protein (W305-mPro1.ECD.mFc) of 5 µg/mL were pre-mixed and incubated with the cells at 4° C. for 1 hour. After washing with 1×PBS/1% BSA, the secondary antibody PE-labeled goat anti-mouse IgG was applied and incubated with cells at 4° C. for 1 hour. Anti-human PD-L1 antibodies BMK8.hIgG4 and BMK9.Fc (IgG1) were used as control antibodies. Human IgG1 and IgG4 isotype antibodies were used as negative control. The cells were then washed and resuspended in 1×PBS/1% BSA. MFI of the cells was measured by a flow cytometer (BD) and analyzed by FlowJo (version 7.6.1).

Figure 2B:
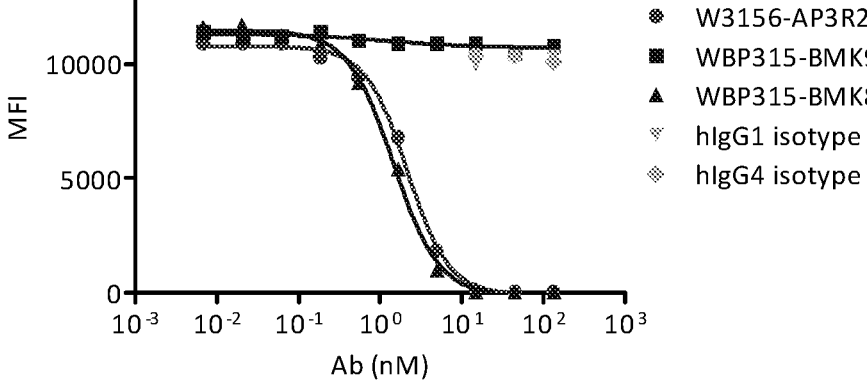
FIG. 2B shows the blockage on the binding of mouse PD-1 to cell surface mouse PD-L1 by anti-PD-L1 antibodies.

Data were shown in FIG. 2B and Table 9.

TABLE 9

| IC50 of the inhibition of binding between mouse PD-1 to PD-L1 | |
| --- | --- |
| Abs | IC50 (nM) |
| AP3R2-1A3-z12-hIgG1 | 2.142 |
| BMK9.Fc (IgG1) | — |
| BMK8.hIgG4 | 1.448 |

4.3 Human PD-L1/CD80 Blocking as Measured by FACS

Human CD80-expressing cells (CHO-K1.CD80.B9) were transferred into 96-well U-bottom plates at a density of $1\times10^5$ cells/well. Various concentrations of antibodies (667 nM, 66.7 nM and 6.67 nM) and constant concentration of human PD-L1 ECD protein (W315-hPro1.ECD.mFc) of 5 μg/mL were pre-mixed for half an hour and incubated with cells at 4° C. for 1 hour. After washing with 1×PBS/1% BSA, the secondary antibody PE-labeled goat anti-mouse IgG was applied and incubated with cells at 4° C. for 1 hour. Anti-human PD-L1 antibodies BMK6.hIgG4, BMK8.hIgG4 and BMK9.Fc (IgG1) were used as positive control. Human IgG1 and IgG4 isotype antibodies were used as negative control. The cells were then washed and resuspended in 1×PBS/1% BSA. MFI of the cells was measured by a flow cytometer (BD) and analyzed by FlowJo (version 7.6.1). Data were shown in FIG. 2C.

As shown in FIG. 2C, AP3R2-1A3-z12-hIgG1 is effective at blocking the binding of human PD-L1 to cell surface CD80 in a dose-dependent manner.

5. Cross-Family Protein Binding Assay as Measured by ELISA 96-well plates were pre-coated with 1 μg/mL, 100 μL per well of human PD-L1 ECD protein (R&D-9049-B7), hPD-L2.ECD.His (SinoBiological-10292-H08H), hCD80.ECD.His (SinoBiological-10698-H08H) or hCD86.ECD.His (SinoBiological-10699-H08H) at 4° C. overnight. After 1-hour blocking using 200 μL of 1×PBS/2% BSA, testing antibodies were added to the plates at a concentration of 66.7 nM. The plate was incubated at ambient temperature for 1 hour. The binding of the antibodies to the immobilized proteins was detected by HRP-labeled goat anti-human IgG antibody. The color was developed by dispensing 100 μL of TMB substrate, and then stopped by 100 μL of 2N HCl. The absorbance was read at 450 nm and 540 nm using a microplate spectrophotometer, respectively. Data were shown in FIG. 3.

As shown in FIG. 3, AP3R2-1A3-z12-hIgG1 specifically human PD-L1 and do not cross-react to PD-L2, CD80 and CD86.

6. Epitope Binning by FACS

Human PD-L1 expressing cells W315-CHO-K1.hPro1.C11 were transferred into 96-well U-bottom plates at a density of $1\times10^5$ cells/well. Various concentrations of W3156 antibody (3-fold serially diluted from 133.3 nM to 0.0068 nM) were mixed with constant concentration of biotinylated BMK6.hIgG4 (0.5 μg/mL) or biotinylated BMK8.hIgG4 (0.5 μg/mL), respectively. Then the mixture was added to the cells in 96-well plates and incubated at 4° C. for 1 hour. After washing with 1×PBS/1% BSA, the secondary antibody SA-PE was applied and incubated with cells at 4° C. for 1 hour. The cells were then washed and resuspended in 1×PBS/1% BSA. MFI of the cells was measured by a flow cytometer and analyzed by FlowJo (version 7.6.1).

In order to test the epitope binning against BMK9, Fc (IgG1), W3156 lead antibody was constructed in a VHH format conjugated with C-myc and His tag. The cells W315-CHO-K1.hPro1.C11 were transferred into 96-well U-bottom plates at a density of $1\times10^5$ cells/well. Constant concentration of AP3R2-1A3 VHH format was mixed with various concentrations of BMK9.Fc (IgG1) (3-fold serially diluted from 133.3 nM to 0.0008 nM), respectively. Then the mixture was added to the cells in 96-well plates and incubated at 4° C. for 1 hour. After washing with 1×PBS/1% BSA, the secondary antibody PE-labeled anti-C-myc was applied and incubated with cells at 4° C. for 1 hour. The cells were then washed and resuspended in 1×PBS/1% BSA. MFI of the cells was measured by a flow cytometer and analyzed by FlowJo (version 7.6.1). Data were shown FIG. 4.

Figure 4:
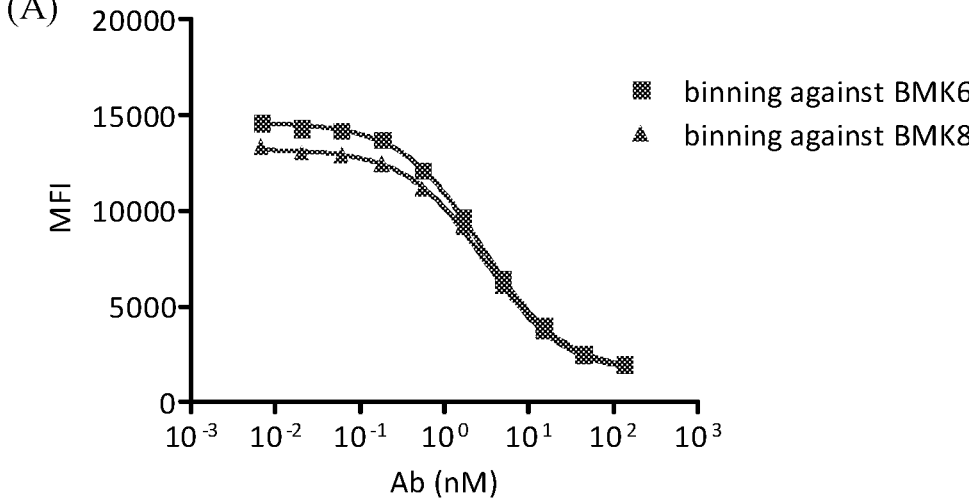
FIG. 4 shows epitope binning of the antibody AP3R2-1A3-z12-hIgG1 against benchmark antibodies: (A) binning against BMK6 and BMK8, and (B) binning against BMK9.
Figure 4:
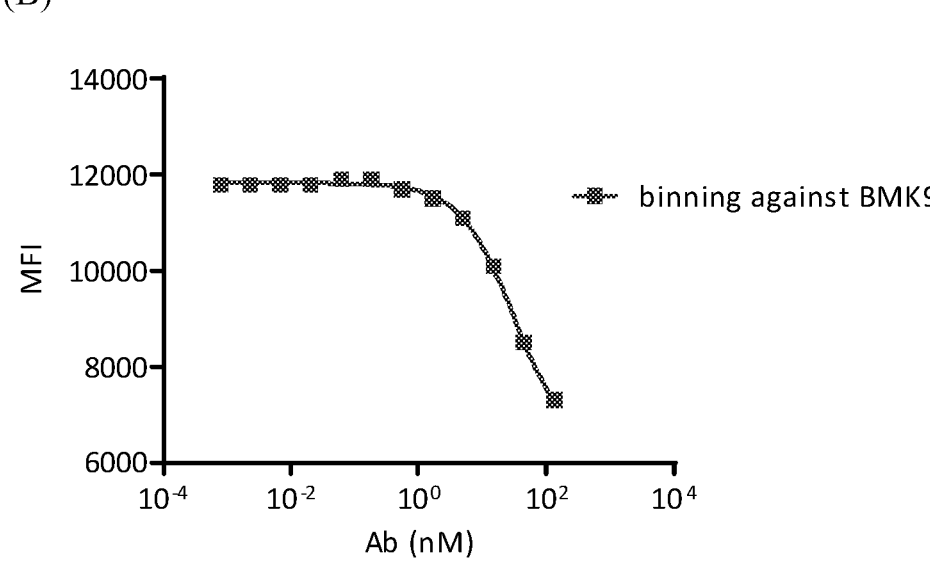

As shown in FIG. 4, AP3R2-1A3-z12-hIgG1 shares similar epitope bin with BMK6, BMK8 and BMK9.

7. Human Cell Based Functional Assays

One-way mixed lymphocyte reaction (one-way MLR) was used to test the agonistic effect of anti-PD-L1 antibodies on cytokine secretion and proliferation of human CD4$^+$ T cells.

i) Cell Isolation, Cell Culture and Induction

Human peripheral blood mononuclear cells (PBMCs) were freshly isolated from healthy donors using Ficoll-Paque PLUS gradient centrifugation. Isolated PBMCs were cultured in complete RPMI-1640 (containing 10% FBS and 1% PS) supplemented with 100 U/mL recombinant human IL-2.

Human monocytes were isolated using Human CD14 MicroBeads kit according to the manufacturer's instructions. Cell concentration was adjusted to $2\times10^6$ cells/mL in complete RPMI-1640 medium supplemented with recombinant human GM-CSF at 800 U/mL and IL-4 at 50 ng/mL. Cell suspension was seeded at 2.5 mL/well in 6-well plate. Cells were cultured for 5 to 7 days to differentiate into dendritic cells (DCs). Cytokines were replenished every 2-3 days by replacing half of the media with fresh media supplemented with cytokines. Eighteen to twenty-four hours before MLR, 1 μg/mL LPS was added to the culture to induce DCs maturation.

Human CD4$^+$ T cells were isolated using Human CD4$^+$ T cell Enrichment kit according to the manufacturer's protocol.

ii) Mixed Lymphocyte Reaction

For human allogeneic MLR, purified CD4$^+$ T cells were co-cultured with allogeneic mature DCs (mDCs).

For human autologous MLR, PBMCs were treated with CMV peptide for 5 days before CD4$^+$ T cell isolation. On the day of assay, DCs were treated with CMV peptide for one hour, and then co-cultured with autologous human CD4$^+$ T cells.

MLR was set up in 96-well round bottom plates using complete RPMI-1640 medium. CD4$^+$ T cells, various concentrations of antibodies (166.7 nM, 66.7 nM, 6.67 nM, 0.667 nM, 0.0667 nM and 0.0067 nM), and allogeneic DCs were added to the plates at an appropriate ratio. The plates were incubated at 37° C., 5% $CO_2$. IL-2 and IFN-γ production was determined at day 3 and day 5, respectively.

iii) Cytokine Detection

Human IFN-γ and IL-2 release were measured by ELISA using matched antibody pairs. Recombinant human IFN-γ and IL-2 were used as standards, respectively. The serial concentrations of IFN-γ was 8, 4, 2, 1, 0.5, 0.25, 0.125, 0.0625, 0.03125 ng/mL, and that of IL-2 was 8, 4, 2, 1, 0.5, 0.25, 0.125, 0.0625, 0.03125 ng/mL. The plates were pre-coated with capture antibody specific for human IFN-γ or IL-2, respectively. After blocking, 50 μL of standards or samples were pipetted into each well and incubated for 2 hours at ambient temperature. Following removal of the unbound substances, the biotin-conjugated detecting antibody specific for corresponding cytokine was added to the wells and incubated for one hour. Streptavidin-HRP was then added to the wells for 30 minutes at ambient temperature. The color was developed by dispensing 50 μL of TMB substrate, and then stopped by 50 μL of 2N HCl. The absorbance was read at 450 nm and 540 nm using a microplate spectrophotometer. The concentration of cytokine in supernatant was calculated from the standard curve. Data were shown in FIGS. 5A, 5B and 5C.

As shown in FIG. 5A, AP3R2-1A3-z12-hIgG1 promotes human CD4$^+$ T cells IL-2 production in a dose dependent way in allogeneic MLR assay. And as shown in FIG. 5B, AP3R2-1A3-z12-hIgG1 promotes CD4$^+$ T cells IFNγ production in a dose dependent manner in allogeneic MLR assay. Further, as shown in FIG. 5C, AP3R2-1A3-z12-hIgG1 promotes CD4$^+$ T cells IFN-γ production in a dose-dependent manner in autologous MLR assay.

8. Mouse Cell Based Functional Assays

One-way MLR was used to test the agonistic effect of PD-L1 antibodies on cytokine secretion and proliferation of mouse CD4$^+$ T cells.

i) Cell Isolation, Cell Culture and Induction

Balb/c and C57BL/6 mice were purchased from Shanghai SLAC Laboratory Animal Co., Ltd.

Mouse bone marrow cells were suspended in complete RPMI-1640 medium supplemented with 20 ng/mL recombinant mouse GM-CSF and 20 ng/mL mouse IL-4. Cell suspension was seeded at 2.5 mL/well in 6-well plate. Cells were cultured for 5 to 7 days to differentiate into DCs. Cytokines were replenished every 2-3 days by replacing half of the media with fresh media supplemented with cytokines. Eighteen to twenty-four hours before MLR, 1 μg/mL LPS was added to the culture to induce DCs maturation.

Mouse CD4$^+$ T cells were isolated from the spleen using Mouse CD4$^+$ T cell Enrichment kit according to the manufacturer's protocol.

ii) Mixed Lymphocyte Reaction

MLR was set up in 96-well round bottom plates using complete RPMI-1640 medium. CD4$^+$ T cells from Balb/c mice, various concentrations of antibodies (166.7 nM, 66.7 nM, 6.67 nM, 0.667 nM, 0.0667 nM and 0.0067 nM), and mDCs from C57BL/6 mice were added to the plates at an appropriate ratio. The plates were incubated at 37° C., 5% $CO_2$. IL-2 production was determined at day 3. The cells were harvest at day 5 to measure CD4$^+$ T cell proliferation by $^3$H-TDR.

iii) Cytokine Detection

Mouse IL-2 release was measured by ELISA using matched antibody pairs. Recombinant mouse IL-2 was used as standards. The serial concentrations of IL-2 were 0.8, 0.4, 0.2, 0.1, 0.05, 0.025, 0.0125, 0.00625, 0.003125 ng/mL. The plates were pre-coated with capture antibody specific for mouse IL-2. After blocking, 50 μL of standards or samples were pipetted into each well and incubated for 2 hours at ambient temperature. Following removal of the unbound substances, the biotin-conjugated detecting antibody was added to the wells and incubated for one hour. Streptavidin-HRP was then added to the wells for 30 minutes at ambient temperature. The color was developed by dispensing 50 μL of TMB substrate, and then stopped by 50 μL of 2N HCl. The absorbance was read at 450 nm and 540 nm using a microplate spectrophotometer. The concentration of cytokine in supernatant was calculated from the standard curve.

iv) Proliferation Detection $^3$H-thymidine was diluted in 0.9% NaCl solution, and added to the cell culture plates at 0.5 uCi/well. Plates were cultured for 16 to 18 hours at 37° C., in a 5% $CO_2$ incubator, before the incorporation of $^3$H-thymidine into the proliferating cells was determined.

As shown in FIG. 6A, AP3R2-1A3-z12-hIgG1 promotes mouse CD4$^+$ T cells mIL-2 production in a dose-dependent manner in MLR assay. And, as shown in FIG. 6B, AP3R2-1A3-z12-hIgG1 promotes mouse CD4$^+$ T proliferation in a dose-dependent way in MLR assay.

9. Antibody-Dependent Cell-Mediated Cytotoxicity (ADCC)

The cells W315-CHO-K1.hPro1.C11 and various concentrations of testing antibodies (10-fold diluted from 66.7 nM to 0.00667 pM) were mixed in 96-well plate, and PBMCs were added at the effector/target ratio of 50:1 (cell number). The plate was kept at 37° C. in a 5% $CO_2$ incubator for 4-6 hours. Target cell lysis was determined by LDH-based cytotoxicity detection kit. Herceptin induced ADCC effect on BT-474 cells was used as positive control. The results for ADCC test were shown in FIG. 7.

Figure 7:
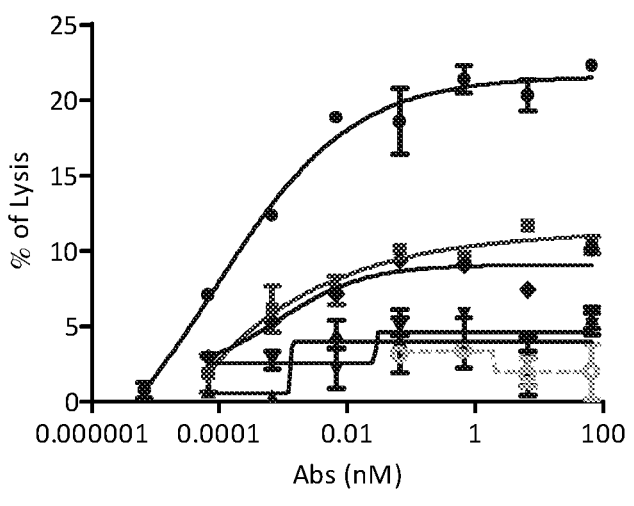
FIG. 7 shows the results of ADCC test of anti-PD-L1 antibodies on PD-L1 transfected cells.

As shown in FIG. 7, AP3R2-1A3-z12-hIgG1 can weakly induce ADCC effect on PD-L1 transfected cells 10. Complement-Dependent Cytotoxicity (CDC)

The cells W315-CHO-K1.hPro1.C11 and various concentrations of testing antibodies (200 nM, 20 nM and 2 nM) were mixed in 96-well plates. Human complement was added at the dilution ratio of 1:50. The plates were kept at 37° C. in a 5% $CO_2$ incubator for 2-3 hours. Target cell lysis was determined by CellTiter-Glo. Rituximab-induced Raji cell lysis was used as positive control. The results for ADCC test were shown in FIG. 8.

Figure 8:
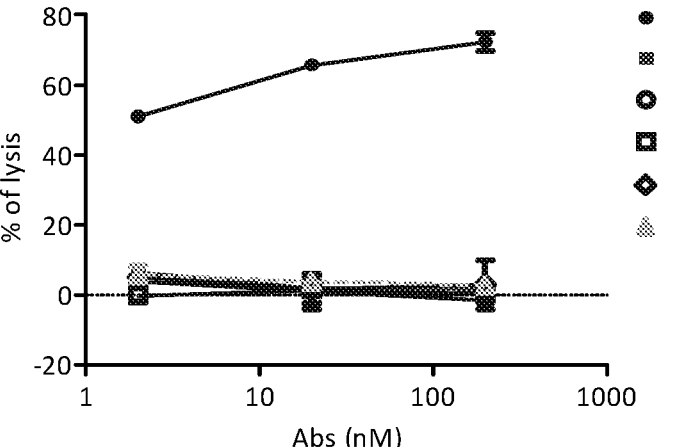
FIG. 8 shows the results of CDC test of anti-PD-L1 antibodies on PD-L1 transfected cells.

As shown in FIG. 8, AP3R2-1A3-z12-hIgG1 does not induce CDC effect.

11. Antibody Stability in Human Serum

Fresh human serum was prepared from healthy donor by centrifugation. Testing antibody was mixed with serum and ensure the serum content >90% of total volume. The mix aliquots were incubated at 37° C. for 0 day, 1 day, 4 days, 7 days and 14 days, respectively. At the indicated time point the samples were quickly-frozen in liquid nitrogen and stored at −80° C. until analysis. The bindings to PD-L1 of the aliquots at above time points were evaluated by flow cytometry, respectively. The results for ADCC test were shown in FIG. 9.

Figure 9:
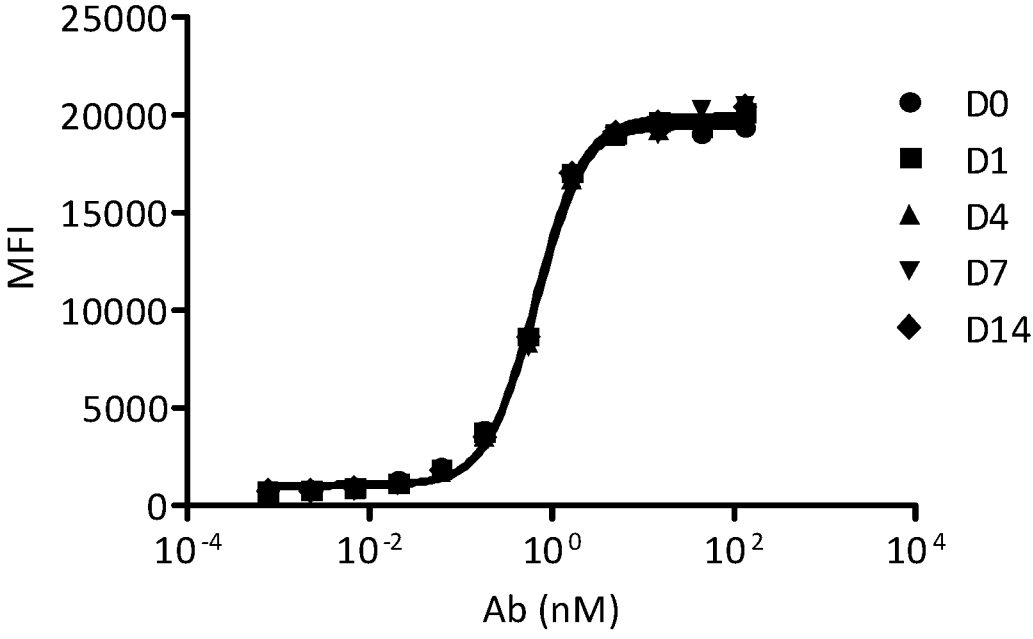
FIG. 9 shows the results of serum stability test, as measured by flow cytometry.

As shown in FIG. 9, AP3R2-1A3-z12-hIgG1 is stable in human serum at 37° C. for at least 14 days.

12. Thermal Stability by DSF Assay

Figure 10:
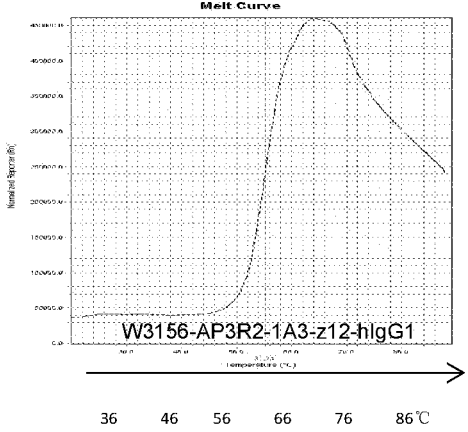
FIG. 10 shows the results of thermal stability test by DSF (Differential Scanning Fluorimetry) assay.

The thermal stability of testing antibody was measured by DSF assay. The DSF assay was performed using 7500 Fast Real-Time PCR system (Applied Biosystems). Briefly, 19 μL of antibody solution was mixed with 1 μL of 62.5× SYPRO Orange solution (Invitrogen) and added to a 96-well plate (Biosystems). The plate was heated from 26° C. to 95° C. at a rate of 2° C./min, and the resulting fluorescence data were collected. The negative derivatives of the fluorescence changes with respect to different temperatures were calculated, and the maximal value was defined as melting temperature Th. If a protein has multiple unfolding transitions, the first two Th were reported, named as Th1 and Th2. Th1 is always interpreted as the formal melting temperature Tm to facilitate comparisons between different proteins. Data collection and Th calculation were conducted automatically by its operation software. Results for thermal stability by DSF assay are shown in FIG. 10 and Table 10.

TABLE 10

| Thermal stability | |
| --- | --- |
| Protein Name | AP3R2-1A3-z12-hIgG1 |
| Isotype | hIgG1 |
| pI | 7.24 |
| Buffer | PBS |
| Concentration (mg/ml) | 4.7 |
| $T_h 1(^\circ C.)$ | 61.2 |

The result shows that AP3R2-1A3-z12-hIgG1 has normal DSF profile and $T_h 1$ is 61.2° C.

13. Non-Specific Binding ELISA

Non-specific binding ELISA was performed in 96-well high binding plates (Nunc-Immuno Plate, Thermo Scientific). The plate was coated with various antigens (as listed in the left column of Table 11) at 2 µg/mL overnight at 4° C. After blocking with 2% BSA-PBS, 10 µg/ml antibodies were added to the plate and incubated for 2 hours. The plates were subsequently incubated with the secondary antibody Goat anti-human IgG Fc-HRP (Bethyl, A80-304P) for additional 1 hour. The HRP signal was detected by adding TMB peroxidase substrate and the reaction was stopped after 12 minutes using 2 M HCl. The absorbance at 450 nm was read using a microplate reader (Molecular Device). All incubation steps were performed at room temperature. The plate was washed with PBST (0.05% Tween20-PBS) between steps. By this test, AP3R2-1A3-z12-hIgG1 does not show non-specific binding. Results are provided in Table 11.

TABLE 11

| Absorbance at 450 nm | Results from Non-specific binding ELISA | | | |
| --- | --- | --- | --- | --- |
| | AP3R2-1A3-z12-hIgG4 | hIgG4K Isotype control | hIgG4L Isotype control | Goat anti-human IgG Fc-HRP |
| Factor VIII | 0.06 | 0.15 | 0.07 | 0.06 |
| FGFR.his | 0.14 | 0.13 | 0.13 | 0.13 |
| CD147.his | 0.07 | 0.06 | 0.06 | 0.05 |
| PD-1.his | 0.06 | 3.29 | 0.05 | 0.05 |
| CTLA4.his | 0.08 | 0.09 | 0.06 | 0.05 |
| W317-hPro1.his | 0.06 | 0.07 | 0.06 | 0.05 |
| CD22.his | 0.06 | 0.06 | 0.06 | 0.05 |
| VEGF.his | 0.09 | 0.11 | 0.08 | 0.06 |
| CD3.his | 0.07 | 0.07 | 0.07 | 0.05 |
| HER3.his | 0.07 | 0.07 | 0.06 | 0.05 |
| OX40.his | 0.06 | 0.06 | 0.06 | 0.05 |
| 4-1BB.his | 0.07 | 0.07 | 0.06 | 0.05 |
| CD40 | 0.25 | 0.25 | 0.24 | 0.24 |
| human serum Albumin | 0.42 | 0.41 | 0.41 | 0.37 |
| Background (No coating) | 0.06 | 0.06 | 0.07 | 0.05 |

Those skilled in the art will further appreciate that the present disclosure may be embodied in other specific forms without departing from the spirit or central attributes thereof. In that the foregoing description of the present disclosure discloses only exemplary embodiments thereof, it is to be understood that other variations are contemplated as being within the scope of the present disclosure. Accordingly, the present disclosure is not limited to the particular embodiments that have been described in detail herein. Rather, reference should be made to the appended claims as indicative of the scope and content of the disclosure.

The invention claimed is:

1. A programmed cell death ligand 1 (PD-L1) binding molecule comprising at least one immunoglobulin single variable domain VHH, wherein the VHH comprises CDR1, CDR2 and CDR3, and wherein CDR1 comprises an amino acid sequence as set forth in SEQ ID NO: 1, CDR2 comprises an amino acid sequence as set forth in SEQ ID NO: 2, and CDR3 comprises an amino acid sequence as set forth in SEQ ID NO: 3.

2. The PD-L1 binding molecule of claim 1, wherein the VHH comprises;

(A) the amino acid sequence as set forth in SEQ ID NO: 4; or (B) an amino acid sequence which is at least 85%, at least 90%, or at least 95% identical to SEQ ID NO: 4 and binds to PD-L1; or (C) an amino acid sequence with addition, deletion and/or substitution of one or more amino acids compared with SEQ ID NO: 4 and binds to PD-L1.

3. The PD-L1 binding molecule of claim 1, wherein the PD-L1 binding molecule is a PD-1 antagonist.

4. The PD-L1 binding molecule of claim 1, wherein the PD-L1 binding molecule is an anti-PD-L1 antibody selected from a single-domain antibody, a chimeric antibody, or a humanized antibody.

5. The PD-L1 binding molecule of claim 1, wherein the VHH is from a camelid animal, comprising an alpaca or a llama.

6. The PD-L1 binding molecule of claim 1, wherein the VHH is fused to another molecule, selected from a group consisting of a Fc domain of an immunoglobin, and a fluorescent protein.

7. The PD-L1 binding molecule of claim 1, wherein the VHH is fused to a Fc domain of IgG.

8. The PD-L1 binding molecule of claim 7, wherein the PD-L1 binding molecule is a chimeric antibody of VHH from a camelid animal and Fc domain of human IgG1 or IgG4.

9. An isolated nucleic acid molecule, comprising a nucleic acid sequence encoding the PD-L1 binding molecule according to claim 1.

10. The isolated nucleic acid molecule of claim 9, comprising a nucleic acid sequence as set forth in SEQ ID NO: 5.

11. An expression vector comprising the isolated nucleic acid molecule of claim 9.

12. A host cell comprising the expression vector of claim 11.

13. A pharmaceutical composition comprising at least one PD-L1 binding molecule according to claim 1 and a pharmaceutically acceptable carrier.

14. A method for preparing the PD-L1 binding molecule according to claim 1, comprising the steps of:

culturing a host cell comprising a nucleic acid sequence encoding the PD-L1 binding molecule according to claim 1 under a condition of expressing the PD-L1 binding molecule in the host cell; and isolating the PD-L1 binding molecule from the host cell.

15. A method for inhibiting or blocking the binding of PD-L1 to PD-1 in a subject, comprising: administering a therapeutically effective amount of the PD-L1 binding molecule according to claim 1 to the subject.

16. A method of treating a condition associated with PD-L1 in a subject, comprising: administering a therapeutically effective amount of the PD-L1 binding molecule according to claim 1 to the subject, wherein the condition associated with PD-L1 is a PD-L1-expressing cancer.

17. The method of claim 16, wherein the cancer is selected from the group consisting of: breast cancer, lung cancer, colon cancer, ovarian cancer, melanoma, bladder cancer, kidney cancer, liver cancer, salivary cancer, stomach cancer, gliomas, thyroid cancer, thymic cancer, epithelial cancer, head and neck cancers, gastric cancer and pancreatic cancer.

18. A kit for treating or diagnosing a condition associated with PD-L1, wherein the kit comprises a container comprising the PD-L1 binding molecule according to claim 1, wherein the condition associated with PD-L1 is a PD-L1-expressing cancer.

* * * * *